United States Patent
Harris, Jr. et al.

(10) Patent No.: US 12,011,179 B2
(45) Date of Patent: Jun. 18, 2024

(54) TIBIAL GUIDE TRANSFER INSTRUMENTS AND METHODS

(71) Applicant: MicroPort Orthopedics Holdings Inc., Arlington, TN (US)

(72) Inventors: Brian R. Harris, Jr., Cordova, TN (US); Robert F. Simes, Jr., Hendersonville, NC (US)

(73) Assignee: MicroPort Orthopedics Holdings Inc., Arlington, TN (US)

(*) Notice: Subject to any disclaimer, the term of this patent is extended or adjusted under 35 U.S.C. 154(b) by 135 days.

(21) Appl. No.: 17/455,945

(22) Filed: Nov. 22, 2021

(65) Prior Publication Data

US 2022/0175398 A1   Jun. 9, 2022

Related U.S. Application Data

(60) Provisional application No. 63/248,059, filed on Sep. 24, 2021, provisional application No. 63/122,115, filed on Dec. 7, 2020.

(51) Int. Cl.
| | | |
|---|---|---|
| *A61B 17/15* | (2006.01) | |
| *A61B 17/17* | (2006.01) | |
| *A61F 2/46* | (2006.01) | |

(52) U.S. Cl.
CPC ........ *A61B 17/157* (2013.01); *A61B 17/1764* (2013.01); *A61F 2/461* (2013.01)

(58) Field of Classification Search
CPC .......................... A61B 17/157; A61B 17/1764
See application file for complete search history.

(56) References Cited

U.S. PATENT DOCUMENTS

| | | | |
|---|---|---|---|
| 1,116,663 A | | 11/1914 | Woodruff |
| 5,306,276 A | * | 4/1994 | Johnson ............... A61B 17/157 606/86 R |

(Continued)

FOREIGN PATENT DOCUMENTS

| | | |
|---|---|---|
| FR | 2742037 A1 | 6/1997 |
| FR | 2810227 A1 | 12/2011 |

(Continued)

OTHER PUBLICATIONS

Wright Medical Technology, Inc. Evolution Medial-Pivot Knee System Surgical Technique, Distal Cut First, Jul. 7, 2013, pp. 1-48, Arlington, TN, USA.

(Continued)

*Primary Examiner* — Sameh R Boles
(74) *Attorney, Agent, or Firm* — Robert J. Hornung

(57) ABSTRACT

Systems, methods, kits, and devices for transferring kinematic alignment references from the distal aspect of a femur to the proximal aspect of an adjacent tibia. An exemplary assembly includes a distally referencing linking drill guide assembly comprising: a linking drill guide comprising: a femoral portion, the femoral portion configured to engage a first femoral engagement member, a tibial portion, the tibial portion configured to engage a first tibial engagement member, and a body connecting the femoral portion to the tibial portion, and a femoral referencing instrument, the femoral referencing instrument having a first complimentary femoral engagement member, wherein the assembly has an engaged configuration when the first femoral engagement member engages the first complimentary femoral engagement member, and wherein the assembly has a disengaged configuration when the first femoral engagement member does not engage the first complementary femoral engagement member.

6 Claims, 28 Drawing Sheets

(56) References Cited

U.S. PATENT DOCUMENTS

| | | | |
|---|---|---|---|
| 5,578,039 | A | 11/1996 | Vendrely et al. |
| 6,013,081 | A | 1/2000 | Burkinshaw et al. |
| 6,059,788 | A | 5/2000 | Katz |
| 6,458,135 | B1 | 10/2002 | Harwin et al. |
| 7,374,563 | B2 | 5/2008 | Roger et al. |
| 7,686,812 | B2 | 3/2010 | Axelson, Jr. et al. |
| 7,794,467 | B2 | 9/2010 | McGinley et al. |
| 8,425,524 | B2 | 4/2013 | Aker et al. |
| 8,444,651 | B2 | 5/2013 | Kunz et al. |
| 8,591,516 | B2 | 11/2013 | Metzger et al. |
| 8,672,945 | B2 | 3/2014 | Lavallee et al. |
| 8,734,453 | B2 | 5/2014 | Tuttle et al. |
| 8,740,910 | B2 | 6/2014 | McMillen et al. |
| 8,974,459 | B1 | 3/2015 | Axelson, Jr. et al. |
| 9,113,957 | B2 | 8/2015 | Axelson, Jr. et al. |
| 9,855,057 | B2 | 1/2018 | Axelson, Jr. et al. |
| 10,130,375 | B2 | 11/2018 | Yager et al. |
| 10,405,871 | B1* | 9/2019 | Bini ............... A61B 17/157 |
| 2007/0173851 | A1 | 7/2007 | McMillen et al. |
| 2008/0161815 | A1 | 7/2008 | Schoenefeld et al. |
| 2008/0275451 | A1* | 11/2008 | McAllister ........ A61B 17/155 623/20.14 |
| 2009/0222014 | A1 | 9/2009 | Bojarski et al. |
| 2010/0121334 | A1 | 5/2010 | Couture et al. |
| 2010/0217338 | A1 | 8/2010 | Carroll et al. |
| 2010/0268240 | A1 | 10/2010 | McGinley et al. |
| 2010/0305575 | A1 | 12/2010 | Wilkinson et al. |
| 2018/0140440 | A1* | 5/2018 | Jackson ............... A61F 2/4684 |
| 2019/0046215 | A1 | 2/2019 | Yager et al. |
| 2019/0336141 | A1* | 11/2019 | Erickson ........... A61B 17/1675 |
| 2021/0000484 | A1* | 1/2021 | Goble ................. A61B 17/164 |

FOREIGN PATENT DOCUMENTS

| | | |
|---|---|---|
| WO | 2012024306 A2 | 2/2012 |
| WO | WO2013057514 A1 | 4/2013 |
| WO | 2016170306 A1 | 10/2016 |
| WO | 2017004669 A1 | 1/2017 |

OTHER PUBLICATIONS

Fernandez Arillo, J., International Search Report for Int'l App. No. PCT/US2021/060444, European Patent Office, mailed Jun. 1, 2022.

Fernandez Arillo, J., Written Opinion of the International Searching Authority for Int'l App. No. PCT/US2021/060444, European Patent Office, mailed Jun. 1, 2022.

* cited by examiner

TIBIAL GUIDE TRANSFER INSTRUMENTS AND METHODS

CROSS REFERENCE TO RELATED APPLICATION

This application claims priority to and incorporates by reference U.S. Provisional Patent Application Ser. No. 63/122,115 filed on Dec. 7, 2020 and U.S. Provisional Patent Application Ser. No. 63/248,059 filed on Sep. 24, 2021.

BACKGROUND OF THE INVENTION

1. Technical Field

The present disclosure relates generally to the field of knee arthroplasties and more particularly to kinematic alignment tibial guide transfer instruments and methods configured to accurately place components of an endoprosthetic knee implant.

2. Related Art

Knee arthroplasties are procedures in which an orthopedic surgeon replaces portions of severely diseased knee joints with an artificial endoprosthetic implant that is intended to restore joint function and alleviate pain. The procedure itself generally consists of the surgeon making a vertical midline anterior incision on the bent knee (i.e., a knee in flexion). The surgeon then continues to incise tissue to access the joint capsule. After the joint capsule is pierced, the patella is moved out of the way and the distal condyles of the femur, the cartilaginous meniscus, and the proximal tibial plateau are exposed.

The surgeon then removes the cartilaginous meniscus and uses instrumentation to measure and resect the distal femur and proximal tibia independently from one another to accommodate the endoprosthetic knee implant. The resections themselves often remove areas of diseased bone and modify the bones' shapes to better accommodate complementary shapes of the respective implant components. That is, the resected distal femur will eventually fit into a complementary femoral implant component and the resected proximal tibia will eventually support a complementary tibial implant component. The surgeon selects from differently sized implant components to match the size of the patient's bones.

There are several schools of thought concerning the angles at which resection of the distal femoral condyles and the proximal tibia should be made. The angles of resection largely determine how the implant components will sit in the joint and can influence how the artificial joint will perform over time.

One such school of thought is the kinematic alignment philosophy. With kinematic alignment, the surgeon seeks to restore the natural pre-diseased joint line of the patient based on data made available to the surgeon both pre-operatively and intra-operatively.

It should come as no surprise that surgical approaches differ even among surgeons who practice kinematic alignment techniques. Some surgeons prefer to use calipers or other measurement instrumentation to measure dimensions of the distal femur and the proximal tibia independently from one another. This approach generally provides the greatest amount of autonomy, which in turn permits the greatest amount of subjectivity and variability in the placement of resection planes (and ultimately, the placement of the implant components). As such, this independently referencing approach can result in the greatest amount of trial and error.

This technique therefore generally prolongs the amount of time that a patient is under a general anesthetic. This technique also increases the risk that the final placement of the joint line will not align with the natural pre-diseased joint line precisely. In extreme cases, non-alignment may encourage supplemental or revision procedures that would have been avoidable otherwise. Even in cases that ultimately place the joint line perfectly, the amount of time required to calculate, resect, install, and test the kinematically aligned joint prolongs the time that the surgical area is exposed. While surgeons typically make every effort to maintain a sterile surgical environment, prolonged procedures nevertheless increase infection risk, prolong blood loss, and can result in more trauma to the surrounding tissue.

Other surgeons may use tools such as the ones disclosed in U.S. Pat. Pub. No. US 2019/0231365 to improve accuracy and to reduce operative times. While certainly an improvement, these tools preserve an element of subjectivity and the risks associated with subjectivity. Setting the tools up and properly adjusting them also adds additional steps to the procedure. In the aggregate, these additional steps may affect the number of patients that the surgeon can see in a day. Instruments with several moving parts can also increase the time needed to sterilize the instruments between procedures.

SUMMARY OF THE INVENTION

As such, there is a long felt, but unresolved need to overcome the disadvantages of the prior art. It is contemplated that the instruments, assemblies, kits, systems, and methods disclosed herein can be used to overcome the disadvantages of the prior art.

The problems of imprecise placement of the resection planes in a knee replacement surgery and of increased procedure time associated with procedures that rely heavily on subjective placement of the resection planes are mitigated by a distally referencing linking drill guide assembly comprising: a linking drill guide comprising: a femoral portion, the femoral portion configured to engage a first femoral engagement member, a tibial portion, the tibial portion configured to engage a first tibial engagement member, and a body connecting the femoral portion to the tibial portion; and a femoral referencing instrument, the femoral referencing instrument having a first complimentary femoral engagement member, the first complimentary femoral engagement member being configured to engage the first femoral engagement member, wherein the distally referencing linking drill guide assembly has an engaged configuration and a disengaged configuration, wherein the engaged configuration comprises the first femoral engagement member engaging the first complimentary engagement member, and wherein the disengaged configuration comprises the first femoral engagement member not engaging the first complimentary femoral engagement member.

It is contemplated that exemplary embodiments described herein can provide improved kinematic knee instruments and methods.

It is further contemplated that exemplary embodiments described herein can provide distal referencing options for transferring alignment to a tibial resection guide.

The foregoing objectives can be achieved by providing kinematic alignment tibial guide transfer instruments and methods having the features described herein.

The foregoing and other objects, features, aspects, and advantages of the invention will become more apparent from the following detailed description of the invention when considered in conjunction with the accompanying drawings.

BRIEF DESCRIPTION OF THE DRAWINGS

The foregoing will be apparent from the following more particular description of exemplary embodiments of the disclosure, as illustrated in the accompanying drawings. The drawings are not necessarily to scale, with emphasis instead being placed upon illustrating the disclosed embodiments.

FIGS. 1-10 generally depict method steps and exemplary devices and assemblies that include an exemplary linking drill guide and that can that involve the use of a femoral trial having complementary femoral engagement members.

FIG. 1 depicts a femoral trial disposed on the distal end of a resected femur.

FIG. 2 depicts threaded femoral linking pins inserted through reference holes in the femoral trial shown in FIG. 1.

FIG. 4 is a perspective view showing the elements from FIGS. 3A and 3B and further depicts a linking drill guide slid over the femoral linking pins with the gap spacers present.

FIG. 8 is another side view of the elements depicted in FIG. 7A in which the tibial posterior slope of the tibial resection guide has been adjusted to match the natural slope of the patient's tibia.

FIG. 9 is a perspective view of the elements depicted in FIG. 7A, wherein the tibial linking pins have been removed and the pivoting tibial resection guide is secured to the proximal tibial through securing pins in securing pin holes.

FIG. 10 is a side view of the elements depicted in FIG. 9, except that the femoral trial has been removed and proximal tibial resection has been performed through a slot in the pivoting tibial resection guide.

FIGS. 11-15 generally depict method steps and exemplary devices and assemblies that include another embodiment of an exemplary linking drill guide and that can involve the use of a distal referencing guide having complementary femoral engagement members.

FIG. 11 is a perspective view of a knee placed in extension, wherein the distal femur has been resected and distal referencing gap spacers have been inserted medially and laterally to fill a joint space between the resected femur and the intact tibia to determine the medial and lateral gap distance.

FIG. 15 is a side view of the elements depicted in FIG. 14C, except that the tibial linking pins have been removed, standard pins have been inserting into standard securing pin holes to fix the orientation of the pivoting tibial resection guide, and proximal tibial resection has been performed through a slot in the pivoting tibial resection guide.

FIGS. 16-28 generally depict method steps and exemplary devices and assemblies that include other embodiments of exemplary linking drill guide and that can that involve the use of a distal femoral resection guide.

FIG. 16 is a perspective view of a knee is flexion wherein the distal femoral resection guide is oriented on the distal femur after the distal cut as been made.

FIG. 18 is a perspective view of a knee in extension in which gap spacers are inserted into the joint space between the resected distal femur and the proximal tibial, wherein an embodiment of the linking drill guide is provided.

FIG. 22 is a side view of the pivoting tibial resection guide disposed on tibial linking pins.

FIG. 23 is a perspective view of the elements depicted in FIG. 21B and further comprising a tibial visual slope gauge with the locking cam in the unlocked position.

FIG. 24 is a side view of the elements depicted in FIG. 23.

FIG. 25 is a side view of the elements depicted in FIG. 23, wherein the pivoting resection guide 40 has been pivoted to adjust the posterior slope of the resection plane.

FIG. 26 is a perspective view of the pivoting tibial resection guide disposed at the desired posterior slope with the locking cam in the locked position.

FIG. 27 is a perspective view of the pivoting tibial resection guide disposed at the desired posterior slope and further depicts a divergent fixation pin extending through the pivoting tibial resection guide to further secure the pivoting tibial resection guide to the tibia at the desired slope.

FIG. 28 is a perspective view of the pivoting tibial resection guide disposed at the desired posterior slope, wherein the tibial plateau has been resected.

DETAILED DESCRIPTION OF THE PREFERRED EMBODIMENTS

Figure 1:
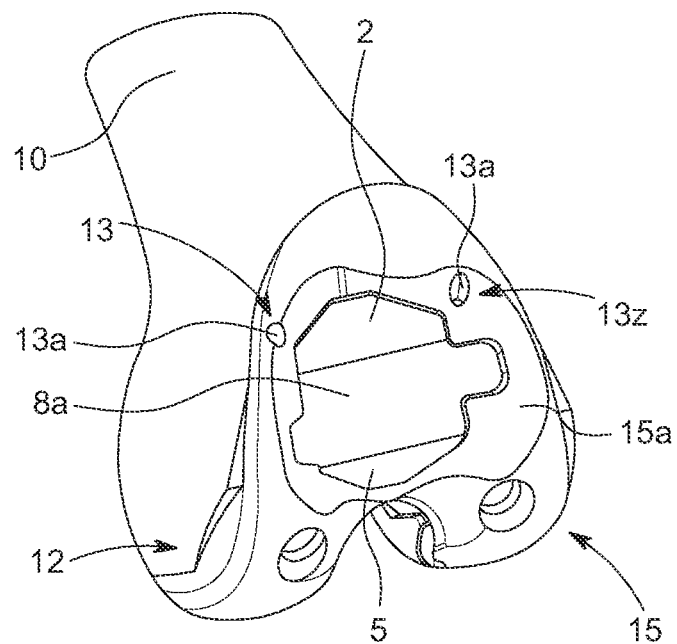

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any sub-ranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

It should be noted that some of the terms used herein are relative terms. For example, the terms, "upper" and, "lower" are relative to each other in location, i.e., an upper component is located at a higher elevation than a lower component in each orientation, but these terms can change if the orientation is flipped. The terms, "inlet" and "outlet" are relative to the fluid flowing through them with respect to a given structure, e.g., a fluid flows through the inlet into the structure and then flows through the outlet out of the structure. The terms, "upstream" and "downstream" are relative to the direction in which a fluid flows through various components prior to flowing through the downstream component.

The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other. The terms, "top" and "bottom" or "base" are used to refer to locations or surfaces where the top is always higher than the bottom or base relative to an absolute reference, i.e., the surface of the Earth. The terms, "upwards" and "downwards" are also relative to an absolute reference; an upwards flow is always against the gravity of the Earth.

There are many reasons that a patient may undergo a total knee arthroplasty ("TKA"). Such reasons may include trauma, the progression of a bone degenerative disease, and excessive wear due to time and robust use. Common bone degenerative diseases include rheumatoid arthritis and arthrosis.

In a primary TKA, (i.e., a TKA in which the surgeon operates on a knee joint that has not previously been operated upon) the surgeon generally makes a vertical midline incision on the anterior side of the operative knee. The incision is generally made with the knee in flexion at or below the tibial tuberosity and may extend several inches above the patella. The surgeon then continues to incise the fatty tissue to expose the anterior aspect of the joint capsule. A medial parapatellar arthrotomy may be performed to pierce the joint capsule and resect the medial patellar retinaculum. A retractor is then commonly used to move the patella laterally to expose the distal condyles of the femur and the cartilaginous meniscus resting on the proximal tibial plateau. The surgeon then removes the meniscus and uses instrumentation to measure and resect the distal femur and proximal tibia. The resected distal femur and the resected proximal tibia will eventually accommodate the endoprosthetic knee implants.

The type of measurement and resection instrumentation used may be influenced by the surgeon's preference for a particular joint placement school of thought. These joint placement schools of thought can influence the designs of available knee endoprosthetic and their associated instrumentation. The three main knee joint placement philosophies are known respectively as anatomic alignment, mechanical alignment, and kinematic alignment.

The oldest alignment school of thought is the anatomic alignment philosophy. In anatomic alignment, the surgeon attempts to resect the tibia at three degrees of varus regardless of the orientation of the patient's actual pre-diseased joint line. Femoral resections and ligament releases are also performed to keep a straight hip-knee-ankle axis of the limb. Releasing the anterior cruciate ligament ("ACL") to accommodate the implant can lead to patient feelings of weakness as described further below. Additionally, implant technology of the time was not yet prepared to handle the effects of the three degree varus resection of the tibia. For example, the varus angle created shear forces between the tibial implant, the meniscal insert, and the femoral implant, which contributed to implant failure.

The angle of resection of the distal femur essentially sets the angle of the axis of the prosthetic joint. Anatomic alignment does not allow the angle of resection to float indefinitely. This can result in an angle of resection that does not align with the native angle of the patient's pre-diseased joint. As a result, anatomic alignment can lead to patient discomfort, weakening of the surrounding soft tissue (e.g., ligaments and muscle) and premature wear of the prosthetic.

In mechanical alignment, the surgeon resects the tibia perpendicular to the mechanical axis of the tibia. The mechanical axis of the tibia generally refers to an axial line extending from the center of rotation of a proximal head of the associated femur through the center of the knee to a center of the ankle. A perpendicular resection of the proximal aspect of the tibia relative to the mechanical axis results in a resection that is coplanar with a transverse plane disposed at the resection area. Many tibial prosthetics designed for mechanical alignment sit on the resected tibial plateau and have articular surfaces configured to place the new joint line parallel to the transverse plane of resection. That is, the reconstructed joint line is also perpendicular to the mechanical axis. Approaching the same concept form a different perspective, a mechanically reconstructed joint line can generally be visualized as being parallel to a flat floor when the knee is in extension and the patient is standing. By contrast, the location of the natural joint line varies from person to person, but on average, the natural joint line has a slight varus tilt relative to a transverse plane of the patient's body.

The mechanical alignment technique can provide good stability when the patient's leg is in extension (e.g., when the patient is standing), and sometimes this technique is required due to trauma or severe disease progression, but the implants that are commonly used with mechanical alignment often require the release of the ACL. In some circumstances, the posterior cruciate ligament ("PCL") may also be released. The ACL normally prevents the tibia from sliding too far anteriorly and from rotating too far relative to the femur. The absence of either of these ligaments can lead to feelings of weakness when the leg is in flexion. Furthermore, changing the location of the patient's natural joint line can lead to feelings of discomfort. Patients who alter their gait to accommodate the new joint line may chronically stress the remaining muscles, which can further exacerbate the feelings of discomfort and contribute to additional musculoskeletal problems in the future.

Resection of the ACL also encourages the use of a "gap balancing" technique in which the surgeon uses a distractor to apply an opposing force to the tibia and the femur in an attempt to set the distal cut surface of the femur parallel to the proximal cut surface of the tibia while symmetrically tensioning the surviving collateral ligaments. The surviving collateral ligaments are typically the lateral collateral ligament ("LCL"), which connects the femur to the fibula on the lateral side, and the medial collateral ligament ("MCL"), which connects the femur to the tibia on the medial side. It is thought that by setting the distal cut surface of the femur parallel to the resected tibial plateau while the distraction forces are evenly balanced on the surviving collateral ligaments, a prosthetic can easily be inserted into the gap disposed between the femur and the tibia. It is thought that the forces of the knee in flexion and extension can be evenly distributed through the prosthetic, thereby avoiding uneven wear and other complications.

However, the anterior profile of the gap is generally trapezoidal after the femoral distal cut has been made. Surgeons are generally taught to create a rectangular gap to accommodate the endoprosthetic implant. To do this, the surgeons commonly release the MCL if the knee is a varus knee, and the LCL if the knee is a valgus knee. Valgus knees are present in a smaller population of patients. The release of these ligaments creates scar tissue as the reattached ligaments begin to heal after a successful procedure. The healed ligament often undergoes contracture as a result of scarring. The ligament release also subjects the tissue to trauma, creates a source of additional bleeding, and can generally prolong patient recovery time.

The newest alignment school of thought is the kinematic alignment philosophy. The kinematic alignment philosophy recognizes that every patient's physiology is slightly different and seeks to restore the patient's natural pre-diseased joint line by taking actual measurements of the operative physiology to ascertain the position of the native joint line. While nothing precludes the use of the present claimed instrument in mechanical or anatomic alignment, the inventors recognized the shortcomings of mechanical and anatomic alignment and invented a device that is also compatible with kinematic alignment.

There are various ways to conduct a kinematic alignment procedure, but all start by referencing the distal condyles of the femur. Most methods involve the evaluation of the thickness of the articular cartilage on the distal aspects of the femoral condyles. Surgeons may use calipers, a cartilage thickness gauge such as the one disclosed in U.S. Pat. Pub. No. 2019/0231365, or other instruments to measure the amount of cartilage wear. The position of the native pre-diseased joint line is largely set by the interaction between the soft tissue (e.g., articular cartilage) on femoral condyles and the tibial plateau as supported by the underlying bone. In the absence of bone loss, knowing the thickness of the pre-diseased cartilage ultimately permits the measurement of the pre-diseased joint line. For example, if the surgeon measured 2 millimeters ("mm") of wear on the medial condyle and no wear on the lateral condyle, and if the surgeon plans to use a 10 mm endoprosthetic implant, the surgeon can set a femoral resection guide on the anterior surface of the femur for the purpose of performing the distal cut of the distal aspect of the femoral condyles. The femoral resection guide can be angled to resect 10 mm of the distal aspect of the lateral condyle and 8 mm of the distal aspect of the medial condyle. The 8 mm of resection on the medial condyle plus the 2 mm of measured cartilage loss will therefore accommodate the 10 mm implant on the medial side. Likewise, the 10 mm resection of the lateral condyle will accommodate the 10 mm implant on the lateral side.

The surgeon then uses a sizing guide or a sizing caliper to size the implant. Surgical kits typically include several implant size options to accommodate variations in the patient population. Once the sizing guide has been used to inform the surgeon of the appropriate implant size, the surgeon then removes the sizing guide and places a four in one cutting block on the resected distal surface of the femur. The four in one cutting block has saw slots that permit the surgeon to make the anterior, posterior, and two chamfer cuts (see FIG. 1).

A femoral implant trial (see 15a) is then placed on the resected distal end 12 of the femur 10. The femoral implant trial 15a desirably matches the sizing dimensions of the endoprosthetic implant that will be later installed. Spreading or traction devices (for example, gap spacers (see 25a, FIG. 4)) are then inserted into the joint gap 3 (FIG. 3A) to measure the medial and lateral dimensions of the joint gap 3.

To determine the amount of proximal tibial resection, the measured dimensions of the medial and lateral aspects of the joint gap are subtracted from the desired thickness of resection. For example, if the surgeon plans to use a 10 mm tibial implant and the medial gap is 3 mm and the lateral gap is 1 mm, the surgeon will orient the tibial resection guide to resect 7 mm of the medial side of the tibial plateau and 9 mm of the lateral side of the tibial plateau. It will be appreciated that in a kinematic alignment technique, the release of the MCL or the LCL is typically unnecessary. If the distal cut surface is not initially parallel to the proximal tibial cut surface, the surgeon typically recuts the tibia until the surgeon has achieved the desirable rectangular-shaped joint gap.

Adjusting the position of the tibial resection guide based on the measurements of the spreading or traction devices creates an angle of resection that has been calculated based upon the patient's particular anatomy. Based upon these measurements, the tibial resection guide is typically oriented at a varus angle relative to the transverse plane, but for some patients, the angle may be valgus or close to 0°. Because of the geometry of the meniscal insert and the femoral component of the endoprosthetic implant assembly, the reconstructed joint line is generally parallel to the plane of tibial resection. Replicating the natural pre-diseased joint line is a significant step in restoring the balanced natural kinematics of the knee. A kinematically balanced knee avoids the problems of the mechanical and anatomic schools of thought.

Described herein are instruments, assemblies, kits, systems, and methods that may be configured to be used in primary total knee arthroplasties ("TKAs").

Linking Drill Guide Technique with Engaging Femoral Trial

FIGS. 1-10 generally depict method steps, exemplary devices, and assemblies that include an exemplary linking drill guide 30 and that can involve the use of a femoral trial having first and a second complementary femoral engagement member 13, 13z.

FIG. 1 is a perspective view depicting a resected distal end 12 of a femur 10. As shown in FIG. 1, the femur 10 is prepared using a preferred resection technique. The distal, anterior/posterior and chamfer cuts are made to form the distal resected surface 5, posterior resected surface 6, anterior resected surface 2, and chamfer resected surfaces 8a, 8b respectively (see also FIG. 7B). The chamfer resected surfaces 8a, 8b comprise the anterior chamfer resected surface 8a and the posterior chamfer resected surface 8b. A four in one cutting block may desirably be used to create the posterior resected surface 6, anterior resected surface 2, and chamfer resected surfaces 8a, 8b, but it will be understood that other instrumentation may be used in lieu of or in addition to the four in one cutting block per the surgeon's preference. A femoral referencing instrument 15 is provided. The depicted femoral referencing instrument 15 is a femoral trial 15a having a first complementary femoral engagement member 13 and a second complementary femoral engagement member 13z in the form of femoral reference holes 13a. Trial implants, such as the depicted femoral trial 15a, are test endoprostheses that generally have the same functional dimensions of the actual endoprostheses, but trial implants are designed to be temporarily installed and easily removed for the purposes of evaluating the fit of the actual endoprostheses and for the purposes of evaluating the knee joint's kinematics. The surgeon generally removes the trial implants and installs the actual implants once the surgeon is satisfied with the trial implant's sizing and the knee joint's kinematics.

In other exemplary embodiments, the femoral referencing instrument 15 can be a distal referencing guide 15b (FIG. 12A), a femoral distal resection guide 15c (FIG. 16), pins 15d (FIG. 17A) or any other instrument disposed on, or associated closely with the distal end 12 of the preferably distally resected surface 5 of the operative femur 10 that can be used directly or indirectly to ascertain the position of the distal aspect of the resected femur 10 relative to the proximal aspect of the tibia 20 of the same leg and, when used in conjunction with an exemplary distally referencing linking drill guide assembly 1 in an engaged configuration, mechanically transfers information about the orientation of the distal resected surface 5 of the femur directly or indirectly to the tibia 20. Stated differently, the femoral referencing instrument 15 can be used to mechanically transfer information about the orientation of the distal resected surface 5 of the femur directly to the tibia 20 (or indirectly through an intermediate instrument such as a pivoting tibial resection guide 40) when the exemplary distally referencing linking drill guide assembly 1 is in the engaged configuration.

Figure 2:
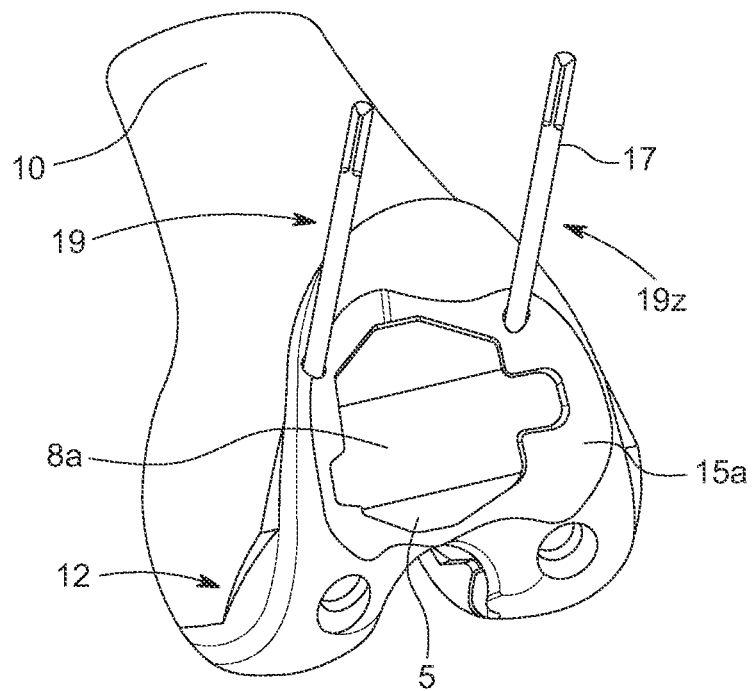

As shown in FIG. 2, each of the femoral reference holes 13a (that is, the example first and second complimentary femoral engagement members 13, 13z) receive a femoral linking pin 17. The leading ends (see the leading end 11 of the divergent fixation pin 34 in FIG. 9 for reference) of these femoral linking pins 17 are in turn placed into the distal portion of the resected femur 10. In the depicted embodiment, the femoral linking pins 17 function as first and second femoral engagement elements 19, 19z.

It will be appreciated that the femoral linking pins 17 may be common pins, headless nails, drill bits, posts, or other connectable fasteners that are compatible with standard pin slots of associated instrumentation such as the distal femoral resection guide 15c (FIG. 16), pivoting tibial resection guide 40 (FIG. 7A), the linking drill guide 30, other drill guides, and other surgical instrumentation. It will also be appreciated that in other exemplary embodiments, the femoral linking pins 17 may have visual or tactile indicators to mitigate surgeon error. Visual indicators can include different colors and markings. Visual and tactile indicators can include raised or recessed portions of the femoral linking pin 17.

Although the exemplary embodiments of FIGS. 1-10 depict a first complementary femoral engagement member 13 and a second complementary femoral engagement member 13z in the form of femoral reference holes 13a, it will be understood that other exemplary embodiments may comprise one complementary femoral engagement member 13. Still other exemplary embodiments may comprise more than two complementary femoral engagement members 13, 13z, etc. The complementary femoral engagement member 13 may take the form of a hole, a slot, a recess, a protrusion, a clamp, a lip, a magnet, a spike, or any other structure known in the art used to selectively (whether directly or indirectly) fixedly engage and disengage one component to another component, and any combination thereof. It will be appreciated that in certain exemplary embodiments, the complementary femoral engagement member 13 may be present in the distal femur 10 itself and the femoral engagement member 19 of the linking drill guide 30 can be configured to engage the complementary femoral engagement member 13 disposed directly in the distal femur 10. In such an exemplary embodiment, the complementary femoral engagement member 13 is likely to be a bore hole disposed directly in the distal femur 10 made by a drill bit guided by a drill guide.

As shown in FIG. 2, femoral linking pins 17 are drilled through the femoral reference holes 13a in the femoral trial 15a. In certain exemplary embodiments, the femoral linking pins 17 may be threaded. In such embodiments, the femoral linking pins 17 are desirably threaded at a leading end (see FIG. 9) to fixedly engage the femoral linking pin 17 into the bone. The femoral linking pins 17 are left in place in the femoral trial 15a.

Figure 3A:
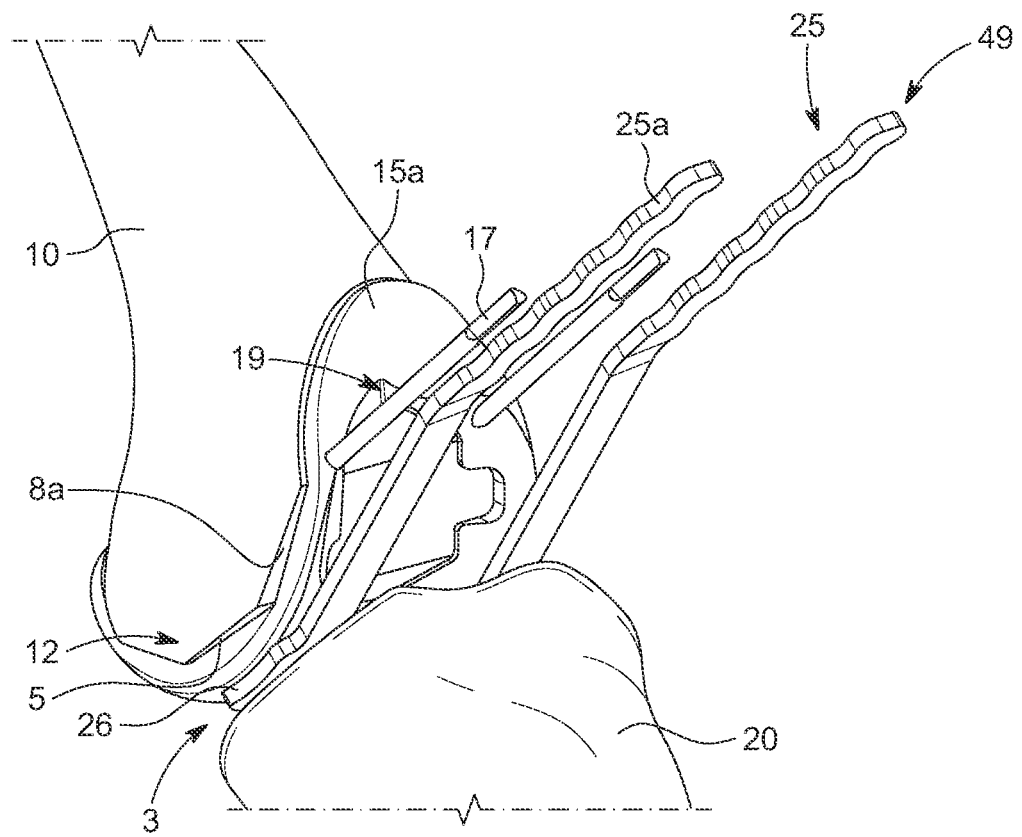
FIGS. 3A and 3B are perspective views of the elements of FIG. 2 and further includes spoon gap spacers inserted medially and laterally between the femoral trial and the tibial plateau of a proximal tibia.
Figure 3B:
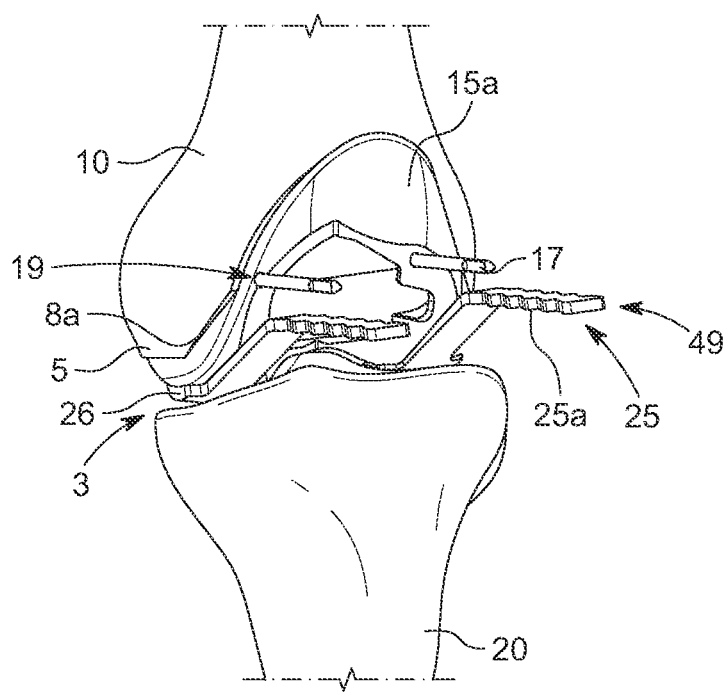

As shown in FIG. 3A and FIG. 3B, spreading devices 49 in the form of gap spacers 25 are inserted medially and laterally to fill the joint gap 3 defined by the area between the distal aspect of the femur 10 and the proximal aspect of the tibia 20. It will be understood that gap spacer 25 can refer to any instrument that can be inserted into the space between the proximal aspect of the tibia and the distal aspect of the femur 10 that is used to measure or otherwise evaluate the size of the joint gap 3 (i.e., the height of the joint gap 3 medially and laterally). In this manner, such spreading devices are "configured to be disposed" between a resected distal femur 10 and a proximal tibia 20 to ascertain a distance between the distal femur 10 and the proximal tibia 20. It will be appreciated that the spreading devices 49 can be disposed in the joint gap 3 when the knee is in flexion or extension.

In the embodiment depicted in FIGS. 3A and 3B, the gap spacer 25 is a spoon gap spacer 25a. The measurement element 26 of the spoon gap spacer 25a is desirably curved to closely abut the curved surface of the femoral trial 15a. It will be understood that many gap spacers 25 having differently dimensioned measurement elements 26 are typically provided for a procedure. The differently sized measurement elements 26 are typically provided in 1 mm height increments, but other increments are contemplated. FIG. 3B shows the measurement element 26 of the medial gap spacer 25 (i.e., the gap spacer 25 depicted on the left side of the image) being thicker than the measurement element 26 of the adjacent lateral gap spacer 25 (i.e., the gap spacer 25a depicted on the right side of the image).

Spoon gap spacers 25a may be provided for the left and right leg. Different embodiments of gap spacers 25 include the snap-on spacers 25b shown in FIG. 6A, differently dimensioned trays or plugs configured to be inserted into the joint space 3, and spacers with removable measurement elements 26. Nothing in this disclosure limits the types of gap spacers 25 that are compatible with the exemplary embodiments of this disclosure.

Furthermore, it will be appreciated that spreading devices 49 can include gap spacers 25, lamina spreaders, a ratcheting tensioner, or other ligament tensioning devices such as gap balancing devices. In certain exemplary methods, traction devices may be used in lieu of or in addition to spreading devices. Whereas spreading devices are typically inserted into the operative area of the knee to separate the distal femur 10 from the proximal tibia 20 at the joint space 3, a tensioning device is typically disposed outside of the operative area, such as on the patient's ankle or leg to pull on the operative leg to thereby provide traction and separate the distal femur 10 from the proximal tibia 20 at the joint space 3. It will be appreciated that a tensioning device can include a boot configured to enclose a portion of the patient's leg, ankle, or foot on the operative leg, a surgeon's or technician's hands, or other device configured to apply traction to the operative leg.

After the distal cut of the femur has been made, the surgeon will selectively insert differently sized spoon gap spacers 25a into the medial and lateral sides of joint gap 3 until the measurement end of the spoon gap spacers 25a provide a secure fit. Without being bound by theory, it is contemplated that the use of a spreading device 49 (such as for example, the spoon gap spacers 25a) in combination with the use of the linking drill guide 30 in the engaged position as described further below, can obviate the need for "gap balancing" and the release of either the MCL or the LCL and thereby avoid the risk of hematoma, unnecessary trauma to the ligaments, scarring, and increased healing time that would otherwise result in a traditional mechanical alignment technique. The spreading device 49 effectively sets the joint gap 3 at the desired distance while the linking drill guide 30 transfers information about the orientation of the distal femoral cut to the tibial resection guide (which can be a pivoting tibial resection guide) to permit the surgeon to quickly make a tibial cut that is usually desirably parallel to the distal femoral cut. The distal femoral cut and the proximal tibial cut effectively define the "rectangle" into which the endoprosthetic implant will be inserted.

Previously, in a mechanical alignment technique, the MCL or the LCL would be released (i.e., cut) to define the "rectangle" into which the endoprosthetic implant would be inserted. In this manner, it is contemplated that the linking drill guide 30 can used to avoid the need for "gap balancing," the release of the MCL or the LCL, and the associated scaring, hematoma, trauma, and increased healing time of traditional methods. These improvements can be especially pronounced when an exemplary linking drill guide 30 is used in a mechanical alignment technique.

It is contemplated that the exemplary embodiments described herein can be used with the mechanical alignment technique, anatomic alignment technique, kinematic alignment technique, or any other technique practiced by a qualified orthopedic surgeon.

Figure 4:
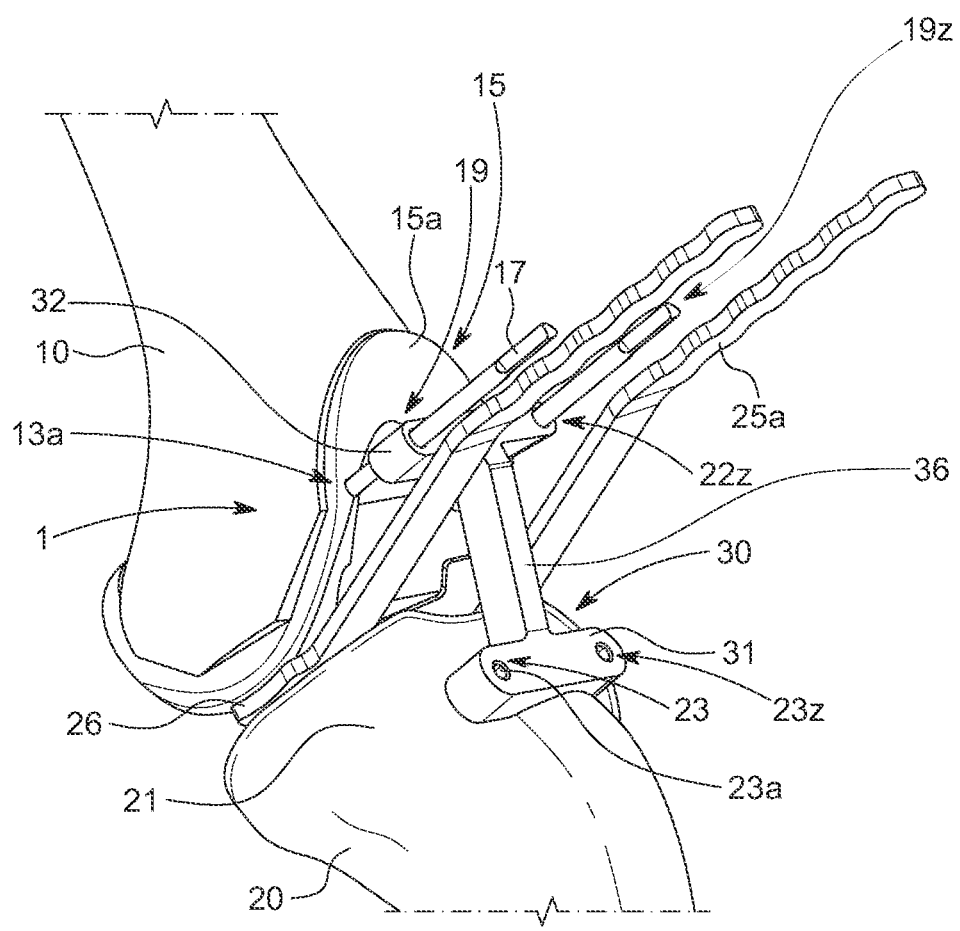

FIG. 4 shows the exemplary distally referencing linking drill guide assembly 1 in the engaged configuration. Exemplary distally referencing linking drill guide assemblies 1 generally comprise a femoral referencing instrument 15 and a linking drill guide 30.

An exemplary linking drill guide 30 has a femoral portion 32, the femoral portion 32 being configured to engage a first femoral engagement member 19. The first femoral engagement member 19 is in turn configured to engage the first complementary femoral engagement member 13 of the femoral referencing instrument 15. The depicted linking drill guide 30 is further configured to engage a second femoral engagement member 19z. The second femoral engagement member 19z is configured to engage the second complementary femoral engagement member 13z (FIG. 1) of the femoral referencing instrument 15. The linking drill guide 30 may be referred to as a "yoke" if desired.

The femoral portion 32 of the linking drill guide 30 has areas defining femoral linking holes 22 (FIG. 5A), 22z. A femoral linking hole 22 is an example structure that permits the femoral portion 32 of the linking drill guide 30 to engage the first femoral engagement member 19. By having a femoral linking hole 22 that can be disposed around the femoral linking pin 17, the linking drill guide 30 can be said to "indirectly engage" the femoral referencing instrument 15 via a first femoral engagement member 19, (which in the depicted embodiment takes the form of the femoral linking pin 17) and first complementary femoral engagement member 13, (which in the depicted embodiment takes the form of a first femoral reference hole 13a (FIG. 1)). In such an exemplary manner, the femoral portion 32 can thereby be said to be, "configured to engage a first femoral engagement member 19."

Likewise, the second femoral linking hole 22z is an example structure that permits the femoral portion 32 to engage a second femoral engagement member 19z. By having a second femoral linking hole 22z that can be disposed around the second femoral linking pin 17, the linking drill guide 30 can be said to "indirectly engage" the femoral referencing instrument 15 via a second femoral engagement member 19z, (which in the depicted embodiment takes the form of the femoral linking pin 17) and second complementary femoral engagement member 13, (which in the depicted embodiment takes the form of a second femoral reference hole 13z). In such an exemplary manner, the femoral portion 32 can thereby be said to be, "configured to engage a second femoral engagement member 19z."

While a femoral linking pin 17 and a femoral linking hole 22 are provided as an example for what may be provided for the femoral portion 32 to be configured to engage a femoral engagement member 19, 19z, etc., it will be appreciated that any mechanical engagement mechanism designed to selectively engage one component to another is considered to be within the scope of this disclosure. Furthermore, while first and second femoral reference holes 13a are provided as an example of a first complementary femoral engagement member 13 and a second complementary femoral engagement member 13z that receive the distal end of the femoral linking pins 17 (e.g., femoral engagement members 19, 19z, etc.) and that are thereby "configured to engage" the femoral engagement members, it will be appreciated that any mechanical engagement mechanism designed to selectively engage one component to another is considered to be within the scope of this disclosure.

It will be also appreciated that in other exemplary embodiments, the first femoral engagement member 19 is an integral part of the linking drill guide 30. For example, the first femoral engagement member 19 may be permanently engaged to the femoral portion 32 and can extend directly from the femoral portion 32 of the linking drill guide 30 (see FIG. 13A and the blade 19c in FIG. 17B). In embodiments where the linking drill guide 30 comprises the first femoral engagement member 19 that is permanently engaged to the femoral portion 32, such embodiments can likewise be said to be, "configured to engage a first femoral engagement member 19." The same can be said for exemplary linking drill guides 30 that comprise a second or even more than two permanently engaged femoral engagement members 19z, etc. A linking drill guide 30 that comprises a permanently affixed femoral engagement member 19, 19z, etc. can further be said to "directly engage" the femoral referencing instrument 15 via a first femoral engagement member 19, and a first complementary femoral engagement member 13.

Likewise, in embodiments where the linking drill guide 30 comprises a second femoral engagement member 19z, such embodiments can likewise be said to be, "configured to engage a second femoral engagement member 19." A linking drill guide 30 that comprises a second femoral engagement member 19z can further be said to "directly engage" the femoral referencing instrument 15 via a second femoral engagement member 19z, and a second complementary femoral engagement member 13z.

In the depicted embodiment, the first and second femoral engagement members 19, 19z are femoral linking pins 17, 17z and the first and second complementary femoral engagement members 13, 13z of the distal femoral referencing instrument 15 are femoral reference holes 13a.

It will be appreciated that in other exemplary embodiments, the first or second femoral engagement member 19, 19z can comprise a slot, a lip, a clamp, hook, protrusion, recesses, spike, magnet, an orientation pin 19b (FIG. 13B), a blade 19c (FIG. 17B), or any other structure known in the art used to directly or indirectly selectively fixedly engage and disengage one component to another component and any combination thereof. In certain exemplary embodiments, the first or second femoral engagement member 19, 19z physically contacts the first complementary femoral engagement member 13 without an intermediary element. In such embodiments, the first or second femoral engagement member 19, 19z can be said to "directly engage" the first or second complementary femoral engagement member 13, 13z. Likewise if an intermediary element is present, the first or second femoral engagement member 19, 19z can be said to "indirectly engage" the first or second complementary femoral engagement member 13, 13z.

The linking drill guide 30 further comprises a tibial portion 31. The tibial portion 31 has areas defining two tibial reference holes 23. It will be appreciated that in certain exemplary embodiments, only one tibial reference hole 23 may be provided. In yet other exemplary embodiments, more than two tibial reference holes 23, 23z may be provided. A body 36 connects the femoral portion 32 to the tibial portion 31. The body 36 of the linking drill guide 30 and the generally parallel disposition of the reference indicia (e.g., the femoral linking holes 22, 22z and the tibial reference holes 23, 23z) on the respective femoral portion 32 and the tibial portion 31, transfers the information regarding the orientation of the plane of distal resection (which is coplanar with the distal resected surface 5) to the tibial portion 31 of the linking drill guide 30. In certain exemplary embodiments, the body 36 may have a fixed length. Multiple linking drill guides 30 each comprising a body 36 that has a length that is different from another body 36 of another linking drill guide 30 provided in a kit may be provided. In such exemplary embodiments, the surgeon may select one linking drill guide 30 of the multiple provided linking drill guides 30 to transfer the information about the distal resected surface 5 of the femur 10 to a tibial resection guide 40 (FIG. 7A) for the purpose of setting the plane of tibial resection. In certain procedures, the plane of tibial resection is desirably parallel to the plane of distal resection.

In other exemplary embodiments, the body 36 can have an adjustable length dimension relative to the femoral portion 32, tibial portion 31, or both the femoral portion 32 and the tibial portion 31. In yet other exemplary embodiments, a length of the femoral portion 32 or the tibial portion 31 can be adjustable relative to the body 36. In any embodiment comprising an adjustment of the length of the linking drill guide 30, the adjustable components are desirably able to be locked at a desired length. It is contemplated that kits that feature such adjustable length linking drill guides may contain fewer linking drill guides 30 than kits that contain multiple linking drill guides 30 having multiple different lengths.

In certain exemplary embodiments, the linking drill guide 30 is provided as a unitary piece. It is contemplated that a unitary piece can be easier to sterilize between procedures and may obviate the risk of mechanical failure compared to exemplary embodiments in which the linking drill guide 30 is not a unitary piece, but rather comprises two or more components. The linking drill guide 30 is desirably sized to be placed anteriorly on the knee exposed in the surgical area. It is contemplated that the exemplary linking drill guides 30 described herein can reduce the overall instrumentation required to preform a TKA, while permitting the surgeon to resect the proximal tibia more quickly than what is safely achievable with existing instrumentation.

Figure 5A:
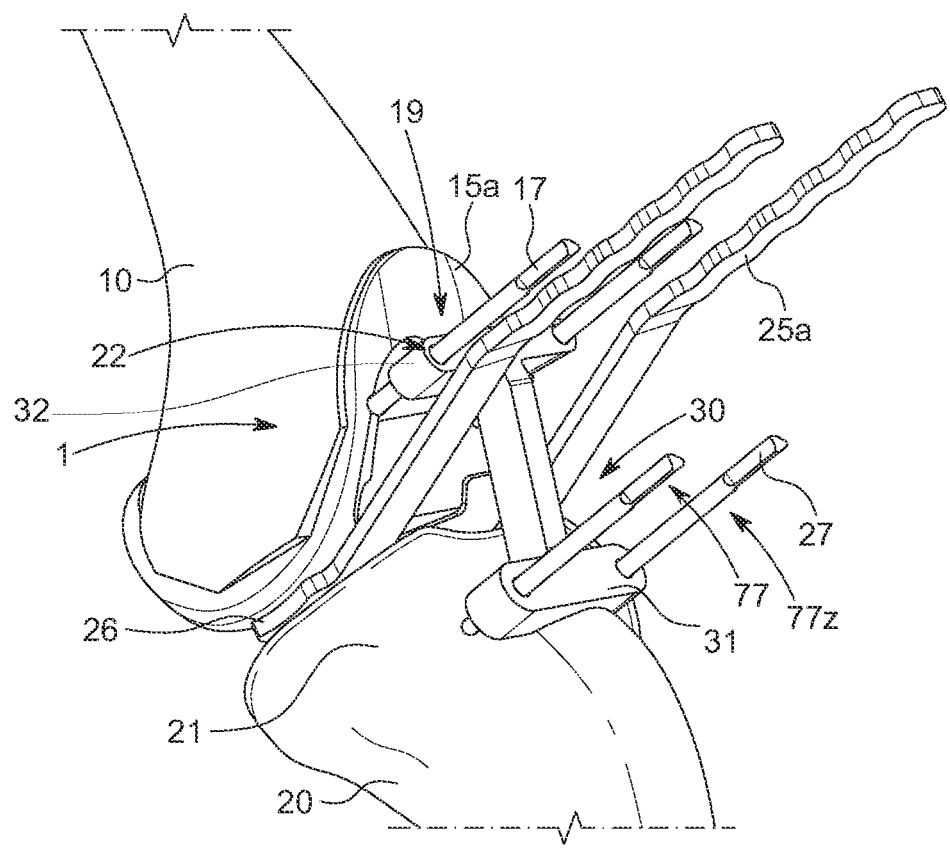
FIGS. 5A and 5B are perspective views of the elements of FIG. 4 further showing tibial linking pins placed in the tibial reference holes in the linking drill guide.

Similarly to the femoral linking holes 22, 22z provided in the femoral portion 32, the first tibial reference hole 23 of the tibial portion 31 permits the tibial portion 31 to engage a first tibial engagement member 77 (FIG. 5A). The depicted embodiment comprises first and second tibial engagement members 77, 77z in the form of the tibial linking pins 27. By having a first tibial reference hole 23 that can be disposed around a tibial linking pin 27, the linking drill guide 30 can be said to be, "configured to engage a first tibial engagement member 77."

Likewise, the second tibial reference hole 23z is an example structure that permits the tibial portion 31 to engage a second tibial engagement member 17z. By having a second tibial reference hole 23z that can be disposed around the second tibial engagement member 77z, the tibial portion 31 can thereby be said to be, "configured to engage a second tibial engagement member 77z."

In the depicted embodiment, the first and second tibial engagement members 77, 77z are tibial linking pins 27, 27z.

It will be appreciated that in other exemplary embodiments, the first or second tibial engagement member 77, 77z can comprise a slot, a lip, a clamp, hook, protrusion, recesses, spike, magnet, an orientation pin, a blade, or any other structure known in the art used to directly or indirectly selectively fixedly engage and disengage one component to another component and any combination thereof. In certain exemplary embodiments, the first tibial engagement member 77 physically contacts the tibia 20 without an intermediary element. In such embodiments, the first tibial engagement member 77 can be said to "directly engage" the tibia 20. It is contemplated that in certain exemplary embodiments, an intermediate element may be disposed between the tibial portion 31 and the tibia 20. In such embodiments, the first or second tibial engagement member 77, 77z may engage the intermediate component and the intermediate component may itself directly engage the tibia 20. In such embodiments, the first or second tibial engagement member 77, 77z can be said to "indirectly engage" the tibia 20.

It is contemplated that exemplary linking drill guides 30 in accordance with this disclosure can be manufactured from (or coated with) any clinically proven biocompatible material, including stainless steel, cobalt chromium alloys, or a plastic polymer such as ultra-high molecular weight polyethylene ("UHWPE"). In certain exemplary embodiments, the linking drill guides 30 can be single-use disposable linking drill guides. In other exemplary embodiments, the linking drill guides 30 can be designed for use in multiple surgical procedures. Regardless of embodiment, the exemplary linking drill guide 30 is desirably sterilized prior to entering the surgical field.

As shown in FIG. 4, a linking drill guide 30 is slid over the femoral linking pins 17 until a tibial portion 31 of the linking drill guide 30 contacts the anterior tibial cortex 21 of the proximal tibia 20. The sliding of the femoral linking holes 22 of the femoral portion 32 over the linking pins 17 extending through the femoral reference holes 13a of the femoral trial 15a in the depicted embodiment defines the engaged configuration of the distally referencing linking drill guide assembly 1. Likewise, it will be appreciated that the distally referencing linking drill guide assembly 1 is in a disengaged configuration when the femoral engagement member 19 is not directly or indirectly engaged to a complementary femoral engagement member 13. In the depicted embodiment for example, the distally referencing linking drill guide assembly 1 is in the disengaged configuration when the femoral linking holes 22 of the femoral portion 32 are not disposed around the linking pins 17.

While femoral linking holes 22 are provided by way of example, it will be appreciated that the femoral linking holes 22 may take the form of a slot, a recess, a tube, a protrusion, a clamp, a lip, a magnet, a spike, or any other structure known in the art used to selectively (whether directly or indirectly) fixedly engage and disengage one component to another component, and any combination thereof. It will also be appreciated that in embodiments wherein the femoral engagement member or members 19, 19z, etc. are integrally engaged to the linking drill guide 30 (see for example, FIGS. 13B and 17B), the femoral linking holes 22 can be absent.

Spreading devices 49 such as gap spacers 25, may be in place prior to sliding the linking drill guide 30 over the femoral linking pins 17, or the spreading devices 49 may be placed in the joint gap 3 after the linking drill guide 30 has been slid over the femoral linking pins 17.

Figure 5B:
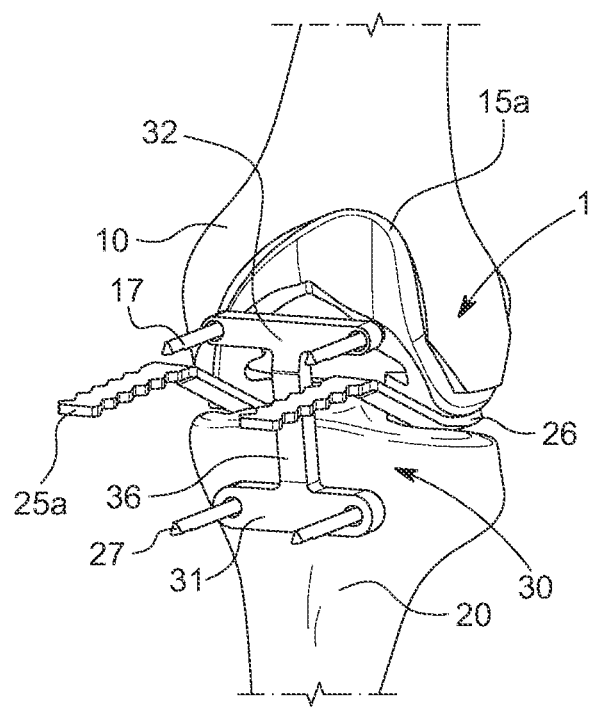

As shown in FIG. 5A and FIG. 5B, with the spoon gap spacers 25a in place, tibial linking pins 27 are placed in each of the tibial reference holes 23, 23z, etc. in the linking drill guide 30. In the depicted embodiment, the tibial reference holes 23, 23z. are tibial drill holes 23a. In other exemplary embodiments, a tibial reference hole 23 can take the form of a hole, a slot, a tube, a recess, a protrusion, a clamp, a lip, a magnet, a spike, or any other structure known in the art used to selectively (whether directly or indirectly) fixedly engage and disengage one component to another component, and any combination thereof. It will also be appreciated that in embodiments wherein the tibial engagement member or members are integrally engaged to the linking drill guide 30, the tibial reference holes 23, 23z can be absent. In certain exemplary embodiments, only one tibial reference hole 23 may be present. The tibial linking pins 27 are secured to the tibia 20. In certain exemplary embodiments, the tibial linking pins 27 are threaded. In such exemplary embodiments, the tibial linking pins 27 are desirably threaded at a leading end 11 (see the leading end 11 of the divergent fixation pin 34 in FIG. 9 for reference) to fixedly engage the tibial linking pin 27 into the tibia 20.

Figure 6A:
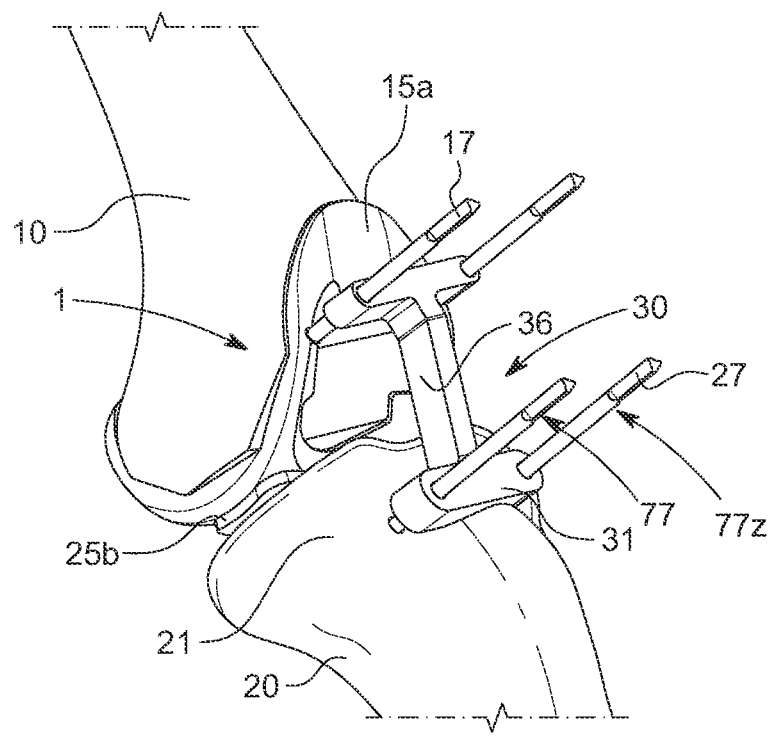
FIGS. 6A and 6B are perspective views depicting the elements of FIGS. 5A and 5B, except that snap-on spacers are disposed between the femoral trial and the tibial plateau instead of the spoon gap spacers.
Figure 6B:
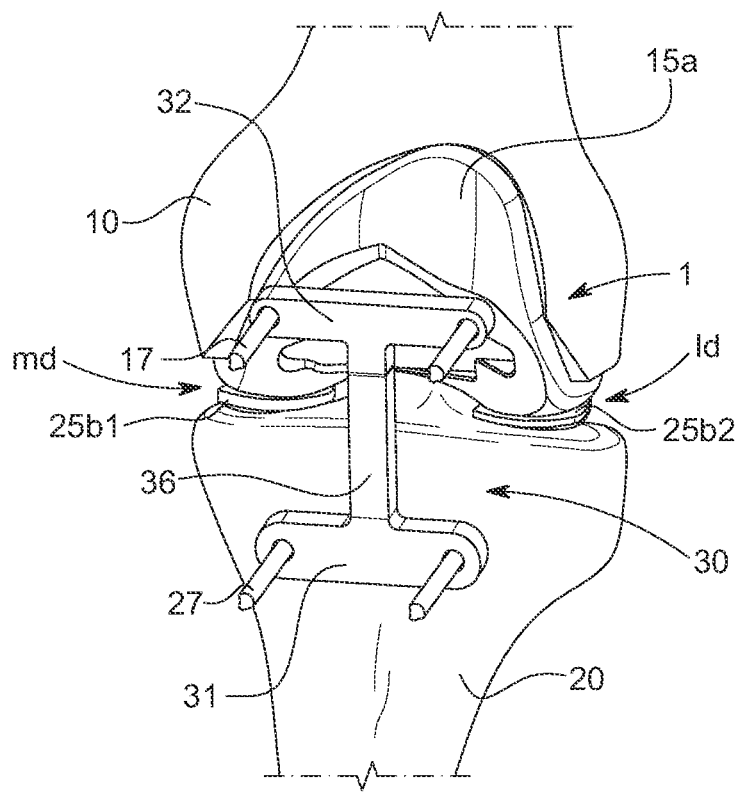

Alternatively, as shown in FIGS. 6A and 6B, snap-on spacers 25b can be used in place of the gap spoons 25a to fill the joint gap 3. It will be appreciated that the measurement element 26 of the snap-on spacers 25b can occupy substantially the same area as the snap-op spacer 25b itself. FIG. 6B provides an illustrative example of the medial snap-on spacer 25b1 being thicker than the adjacently disposed lateral snap-on spacer 25b2.

Figure 7A:
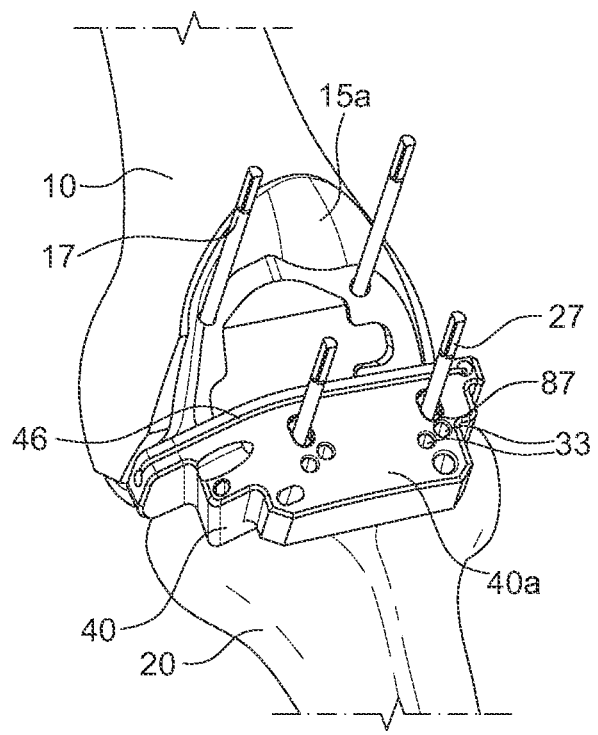
FIG. 7A is a perspective view depicting the elements of FIGS. 6A and 6B, wherein the linking drill guide has been removed and a pivoting tibial resection guide has been slid onto the tibial linking pins.

As shown in FIG. 7A, the linking drill guide 30 is removed, leaving the femoral linking pins 17 in place in the femur 10 and the tibial linking pins 27 in place in the tibia 20. The receiving slots 87 of a pivoting tibial resection guide 40 are slid over the tibial linking pins 27. In the depicted embodiment, the receiving slots 87 extend generally anteriorly-posteriorly through the body 40a of the pivoting tibial resection guide 40. The receiving slots 87 are desirably sized to closely encompass the medial-lateral width of the tibial linking pins 27 while having a generally vertical (i.e. superior to inferior) length dimension that permits the pivoting tibial resection guide 40 to pivot around the tibial linking pins 27 as described further below.

Figure 30:
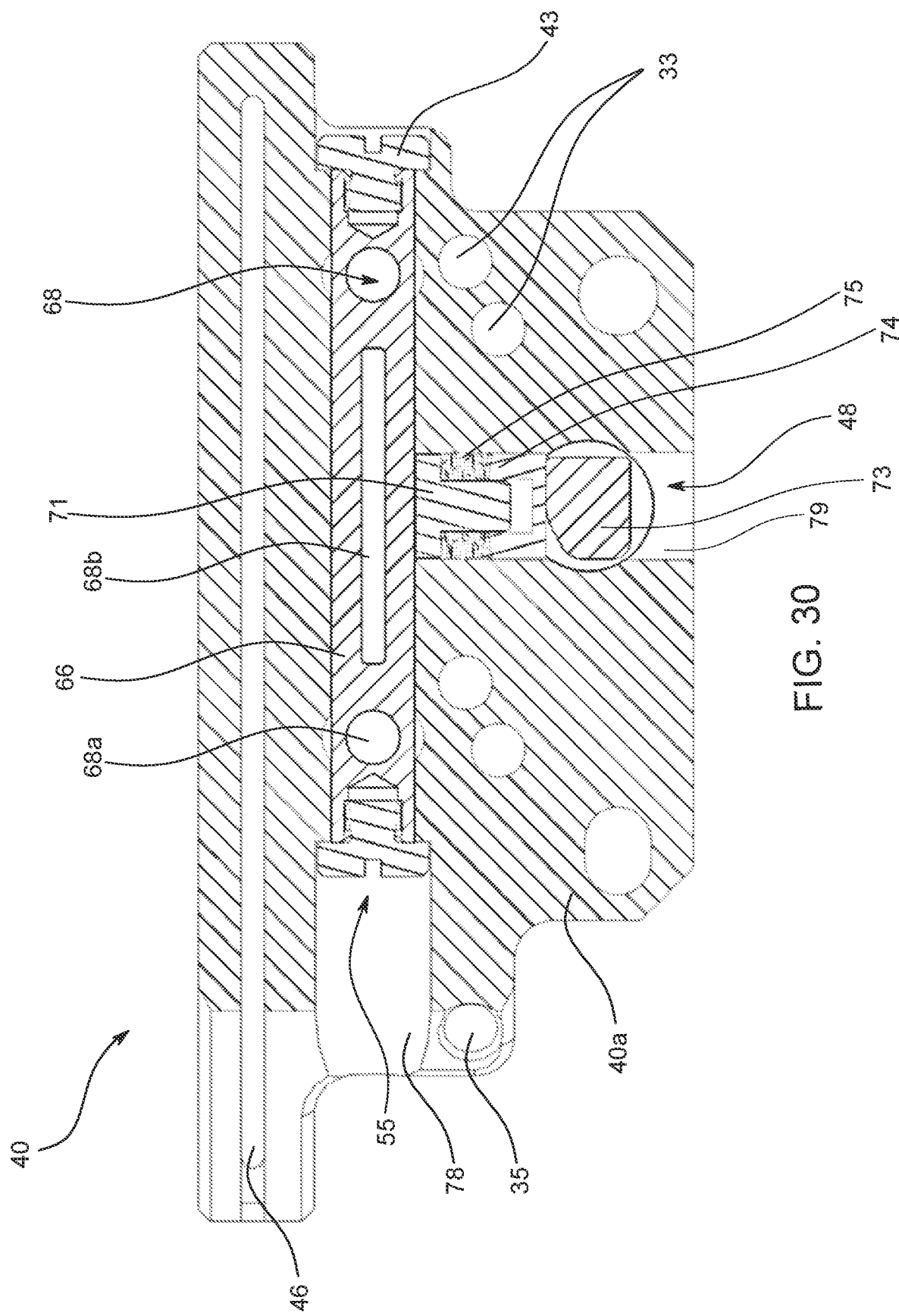
FIG. 30 is an anterior cross-sectional view of an exemplary pivoting tibial resection guide.

FIG. 30 is a cross-sectional anterior view of an exemplary pivoting tibial resection guide 40. The pivoting tibial resection guide 40 can comprise a pivoting tibial resection guide body 40a. The body 40a defines a generally linear resection slot 46 disposed above a pivoting recess 78. A pivoting assembly 55 can be closely dimensioned to rotate axially within the pivoting recess 78. The pivoting assembly 55 itself is disposed above a locking mechanism recess 79 that is preferably dimensioned to closely enclose a locking mechanism 48. The body 40a further has areas defining multiple standard holes 33, +2 mm standard pin holes 33, and a divergent fixation pin receiving hole 35.

The depicted locking mechanism 48 comprises a cam 73, a cam follower 74, a shaft 71 substantially perpendicularly oriented to a pivoting guide 66 and springs 75 disposed between the cam follower 74 and the shaft 71. The pivoting assembly 55 comprises a pivoting guide 66 and end screws 43 placed on either end of the pivoting guide 66 prevent the pivoting guide 66 from sliding out of the pivoting tibial resection guide 40. The pivoting guide 66 desirably has one or more complimentary tibial engagement members 68 that can receive a tibial engagement member associated with the drill linking guide 30. Complimentary tibial engagement members 68 may include a slot 68b dimensioned to receive the linking tab 64 of the spike plate 67 (see the embodiment depicted in FIG. 20B) and tibial engagement holes 68a disposed adjacent to either lateral side of the slot 68b. However, in certain exemplary embodiments, either one or more tibial engagement holes 68a may be provided in lieu of the slot 68b and vice versa.

Figure 7B:
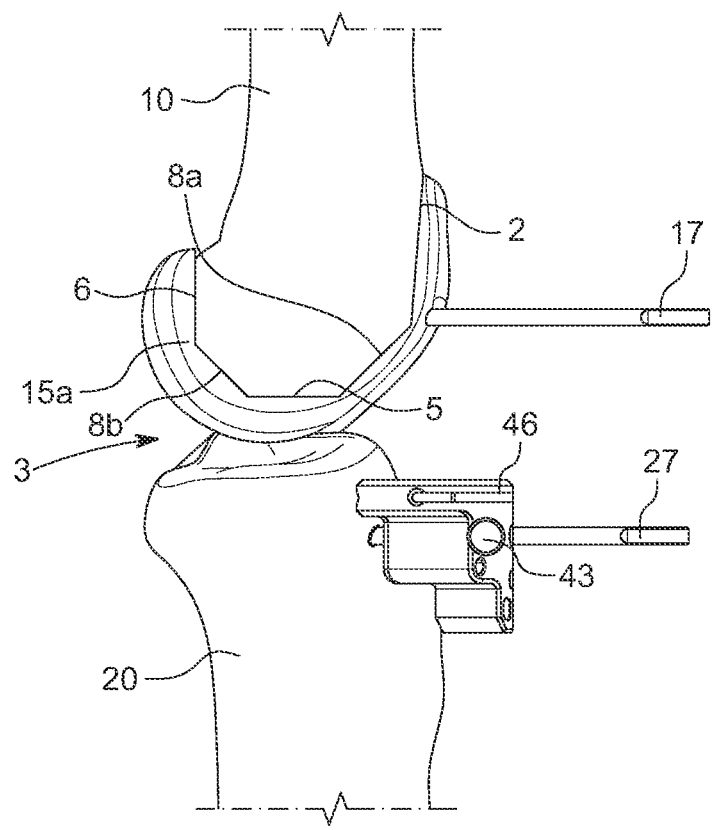
FIG. 7B is a side view of the elements depicted in FIG. 7A.
Figure 29:
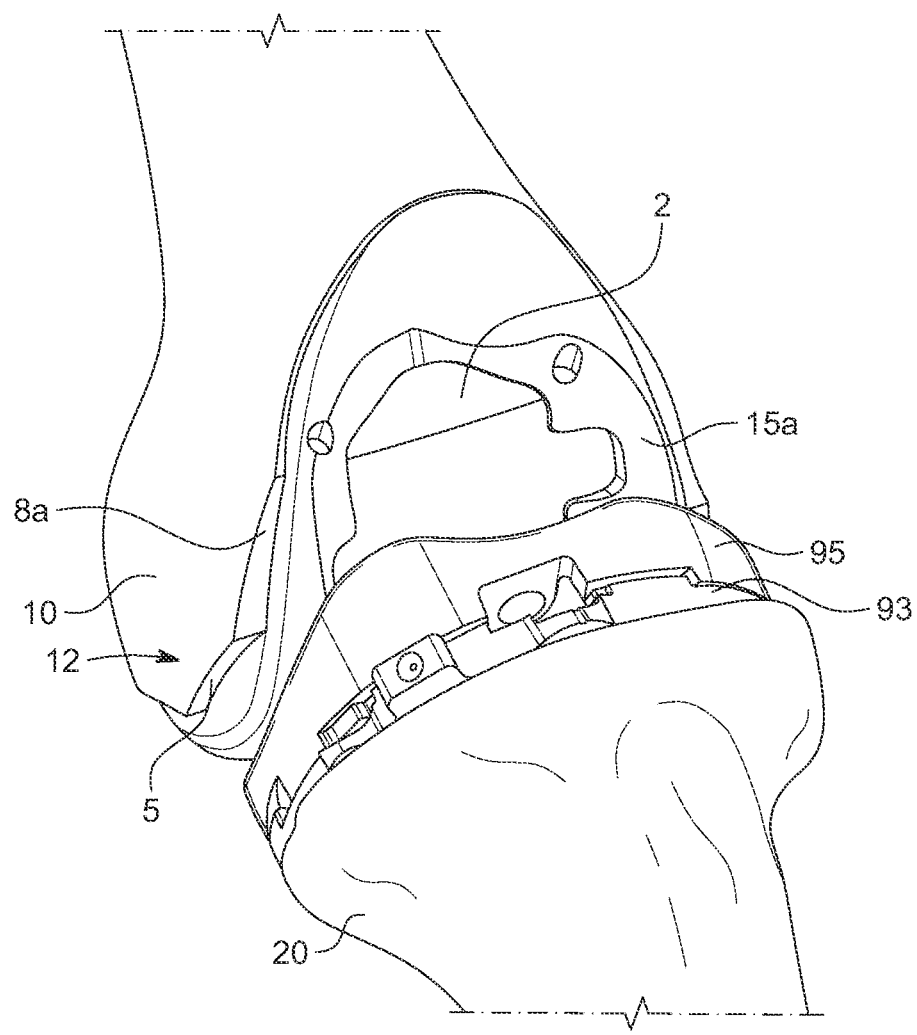
FIG. 29 is a perspective view of a femoral trial, tibial base trial and meniscal insert based on sizing criteria.

As shown in the side view of FIG. 7B, the tibial resection level is set automatically to accommodate a 10 mm tibial component (or construct) of an endoprosthetic assembly, which can comprise a tibial trial base 93 (FIG. 29) and a meniscal trial insert 95 (FIG. 29). In embodiments, the linking drill guide 30 can be made to allow for other resection levels as needed or desired by the surgeon, such as by a plurality of linking drill guides 30, multiple pin holes on the linking drill guide 30, multiple linking holes on the pivoting tibial resection guide 40, or an adjustable linking drill guide 30.

Figure 8:
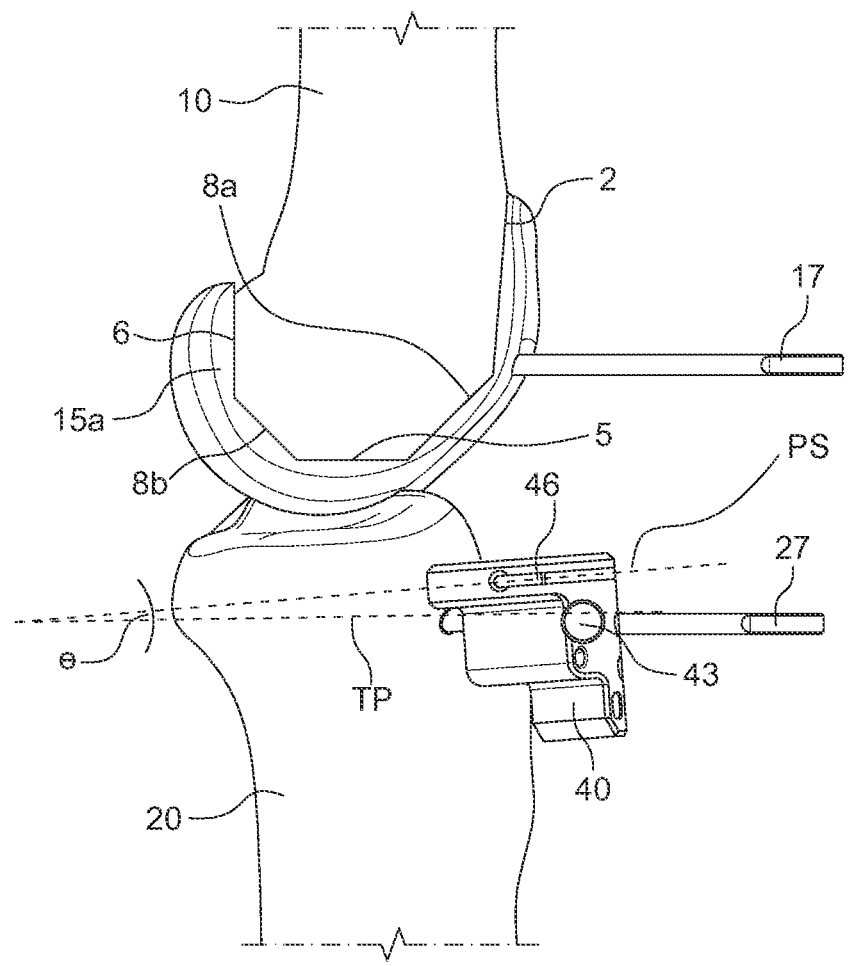

As shown in FIG. 8, the tibial posterior slope PS can be adjusted as needed to match the natural anatomy. The pivoting tibial resection guide 40 is configured such that the pivoting tibial resection guide 40 can be adjusted relative to the placement of the tibial linking pins 27 in the tibia 20. The tibial posterior slope PS can be imagined as a plane extending generally anteriorly-posteriorly and medially and lateral that passes through the resection slot 46. In FIG. 8, the side view of this plane is depicted as a line. The intersection of the tibial posterior slope PS and a transverse plane TP extending generally horizontally through the tibia 20 defines the posterior slope angle θ. The placement of the transverse plane TP can be measured from any frame of reference that is useful to define the posterior slope angle θ. In the depicted embodiment, the transvers plane TP is disposed coplanar with the tibial linking pins 27 extending into the tibia 20. In the side view of FIG. 8, the transverse plane TP is represented as a line. In embodiments, the pivoting tibial resection guide 40 can be adjusted from about minus 3 degrees to about plus 10 degrees relative to the tibial linking pins 27. Once the desired tibial posterior slope PS is reached, the pivoting tibial resection guide 40 can be locked in place using a locking mechanism 48 on the pivoting tibial resection guide 40.

Figure 9:
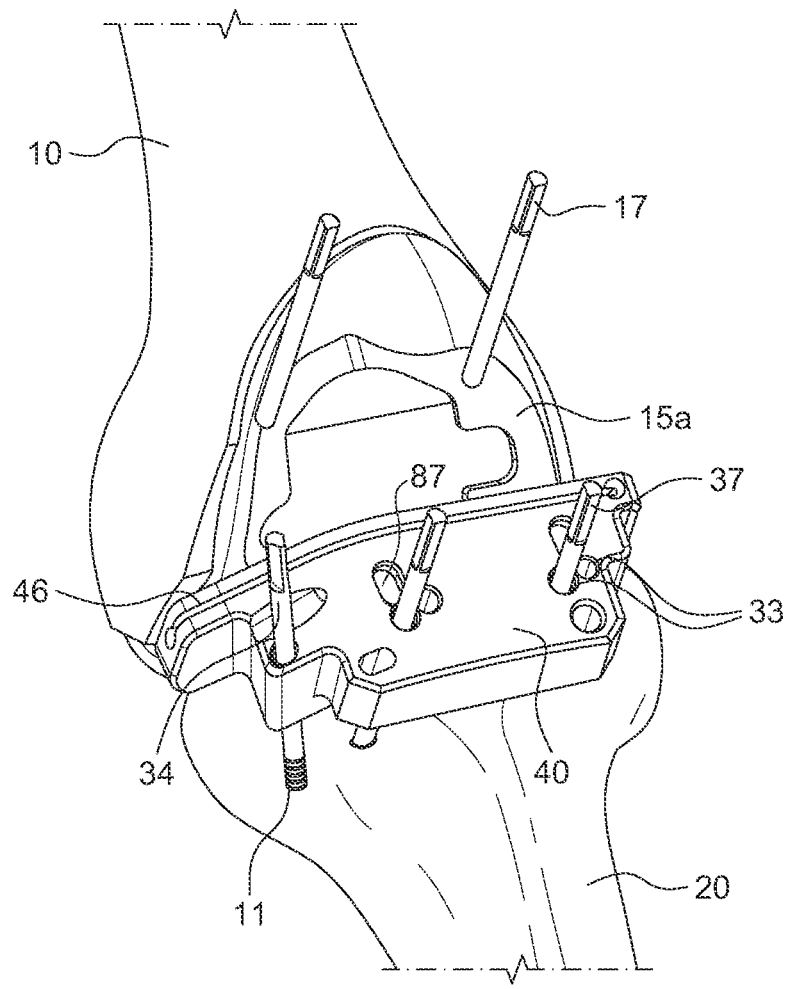

As shown in FIG. 9, once the posterior slope PS is set at the desired posterior slope angle θ, the pivoting tibial resection guide 40 is pinned in place by inserting pins 37 through standard pin holes 33 and into the tibia 20. The standard pins holes 33 depicted include the 10 mm pin holes disposed below and slightly offset from the +2 mm standard pin holes 33. The pins 37 extend through the standard pin holes 33 in FIG. 9. The +2 mm standard pin holes 33 can be used if the sizing guide indicates that that patient's anatomy would require a tibial construct (i.e., meniscal trial insert 95, and tibial trial base 93, see FIG. 29) greater than the standard 10 mm. In common practice however, the pivoting tibial resection guide 40 is more likely to be replaced back onto the pins 37 in the +2 mm standard pin holes 33 if the amount of tibial resection was insufficient to allow for a 10 mm tibial construct. It will be appreciated that other exemplary pivoting tibial resection guides 40 can have more than four pin holes 33. All practicable increments between standard pin holes 33 are considered to be within the scope of this disclosure.

In FIG. 9, the tibial linking pins 27 have been removed from the receiving slots 87 of the pivoting tibial resection guide 40. The pins 37 extend through the standard pin holes 33 into the tibia 20 generally prohibit further pivoting.

Rather, these pins 37 can be used to fix the pivoting tibial resection guide 40 in the desired orientation. As shown, a divergent fixation pin 34 can be used if desired for added stability. The leading end 11 of the divergent fixation pin 34 extends into the anterior tibial cortex 21 of the proximal tibia 20.

As illustrated with reference to FIG. 9, other resection levels of the proximal tibia 20 can also be realized with a plurality of standard pin holes 33 disposed at different resection levels. Sliding the standard pin holes 33 disposed at different elevations of the pivoting tibial resection guide 40 over resection levels changes the position of the resection slot 46 superiorly and inferiority relative to the top of the tibial plateau and thereby permits the surgeon to adjust the amount of resection to accommodate endoprosthetic implant assemblies of different sizes.

Figure 10:
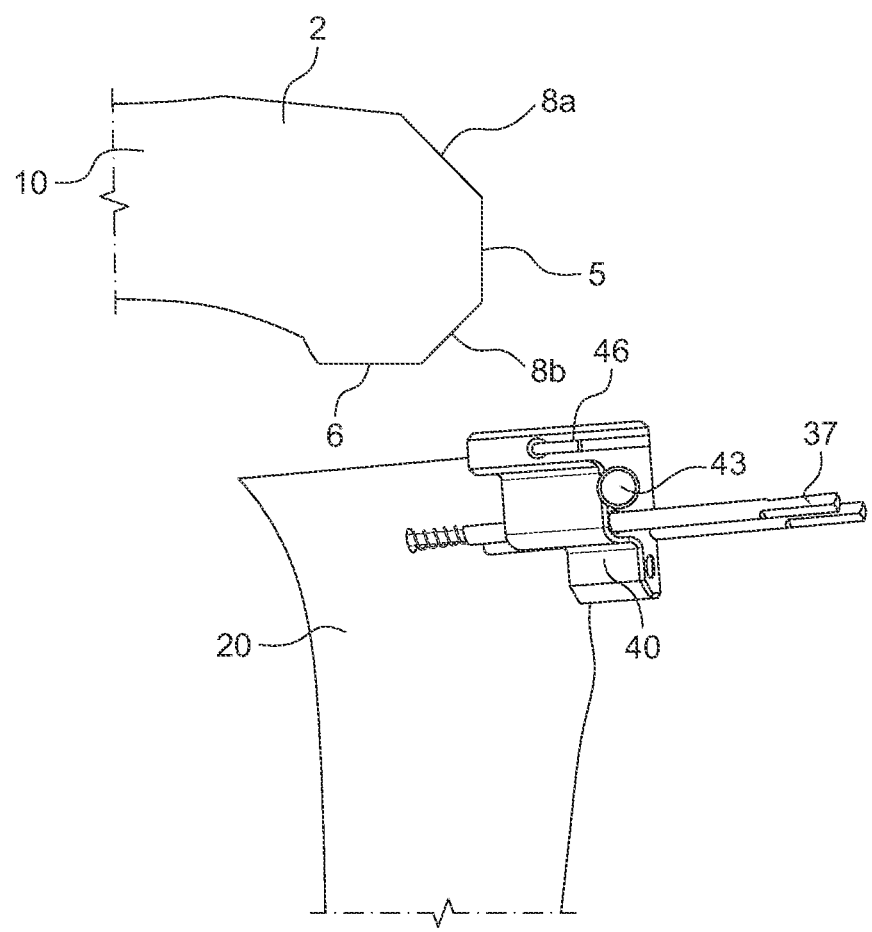

As shown in FIG. 10, the femoral trial 15a is removed and a proximal tibial resection is performed through the resection slot 46 in the pivoting tibial resection guide 40. The surgeon typically uses a handheld surgical saw inserted through the resection slot 46 to make the resection. In other exemplary embodiments, the surgeon can use the top of the pivoting tibial resection guide 40 as a plane upon which to align the proximal tibial resection.

Once the tibial resection is complete, the surgeon selects an appropriate size tibial trial base 93 and meniscal trial insert 95. The femoral trial 15a is then re-placed on the resected distal end 12 of the femur 10 and a trial reduction is carried out. The femoral sulcus, peg prep, and tibial keel prep can be performed according to a kinematic alignment technique or surgeon preference.

Distal Referencing Technique

FIGS. 11-15 generally depict method steps and exemplary devices and assemblies that include another exemplary linking drill guide 30, wherein the femoral referencing instrument 15 is a distal referencing guide 15b having complementary femoral engagement members 13.

Figure 11:
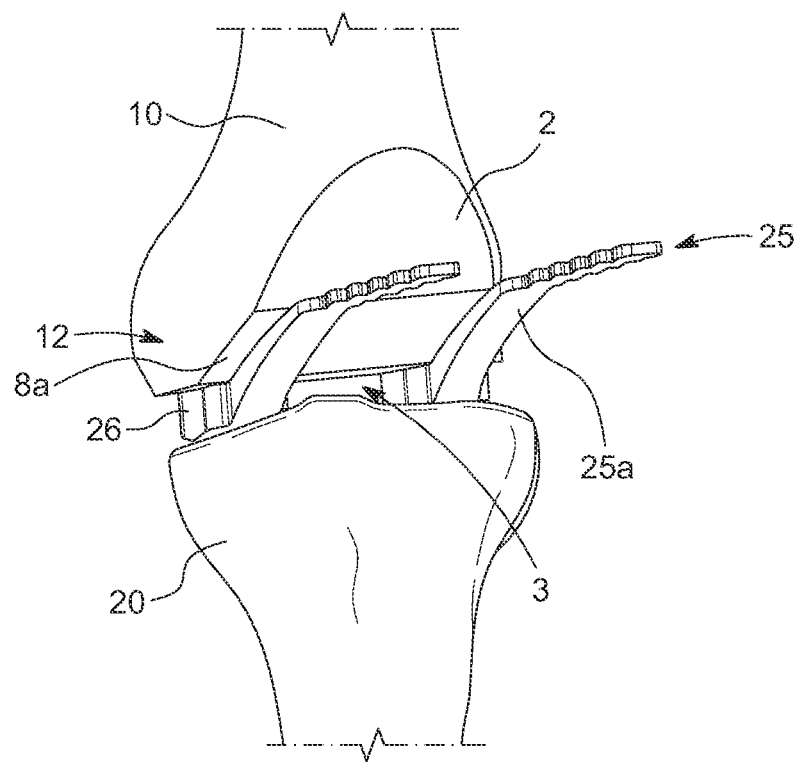

FIG. 11 is a perspective view of a knee placed in extension, wherein the distal femur 10 has been resected and spoon gap spacers 25a have been inserted medially and laterally to fill a joint space between the resected femur 10 and the intact tibia 20 to determine the medial and lateral gap distance. The surgeon or technician will then select snap-on spacers 25b out of many available snap-on spacers 25b, wherein a first snap-on spacer has a thickness that is different from another available snap-on spacer 25b. Once selected thicknesses snap on spacers 25b of an appropriate thickness are selected, the fully assembled distal referencing guide 15b matches the gap distance d determined in the step using the spoon gap spacers 25a (see FIG. 11).

In certain exemplary methods, the use of the spoon gap spacers 25a can be omitted, and the distal referencing guide 15b with snap-on gap spacers 25b that are selectively chosen to match the distance of the medial and lateral dimension of the joint gap 3 can be used in lieu of the spoon gap spacers 25a.

In certain exemplary methods, the pivoting tibial resection guide 40 can also be used in a distal referencing technique. At the beginning of the distal referencing technique, the distal end 12 of the femur 10 is resected. The distal, anterior, posterior, and chamfer cuts are made to form the distal resected surface 5, posterior resected surface 6, anterior resected surface 2, and chamfer resected surfaces 8a, 8b respectively (see also FIG. 14B). U.S. Pat. App. Pub. No. 2019/0231365A1, which is incorporated herein by reference, provides one example of how a surgeon may orient the distal, anterior, posterior, and chamfer cuts. As shown in FIG. 12B, after the distal resection, the knee is placed in extension and distal referencing guide 15b is inserted into the joint space 3. In the depicted embodiment, the distal referencing guide 15b comprises a distal referencing portion 44, a modular handle 41, and snap-on gap spacers 25b disposed on a bottom side of the distal referencing portion 44.

Figure 12A:
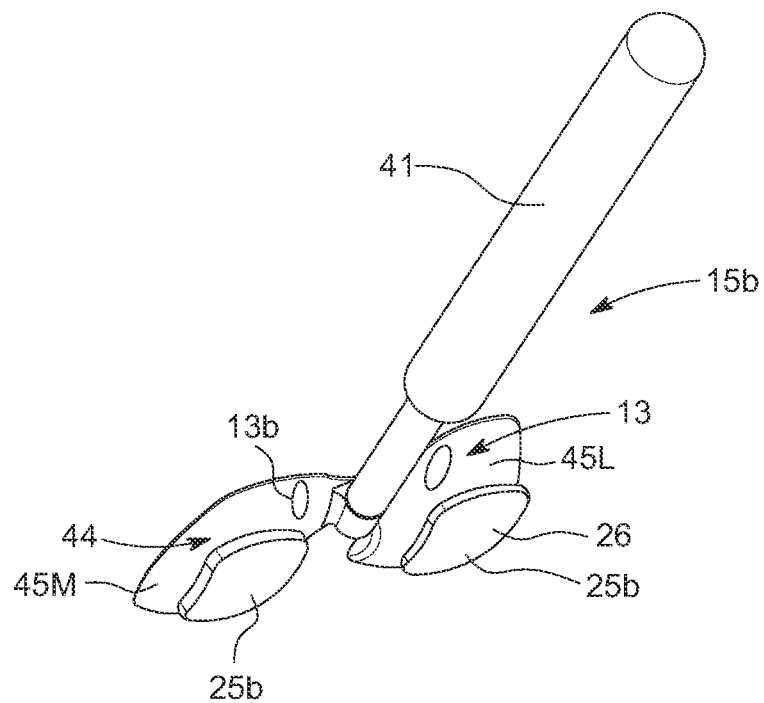
FIG. 12A is a perspective view of a distal referencing guide having a removable handle connected to a femoral portion comprising a medial condylar portion and a lateral condylar portion, wherein a distal portion of each of the condylar portions is configured to receive a snap on spacer.
Figure 12B:
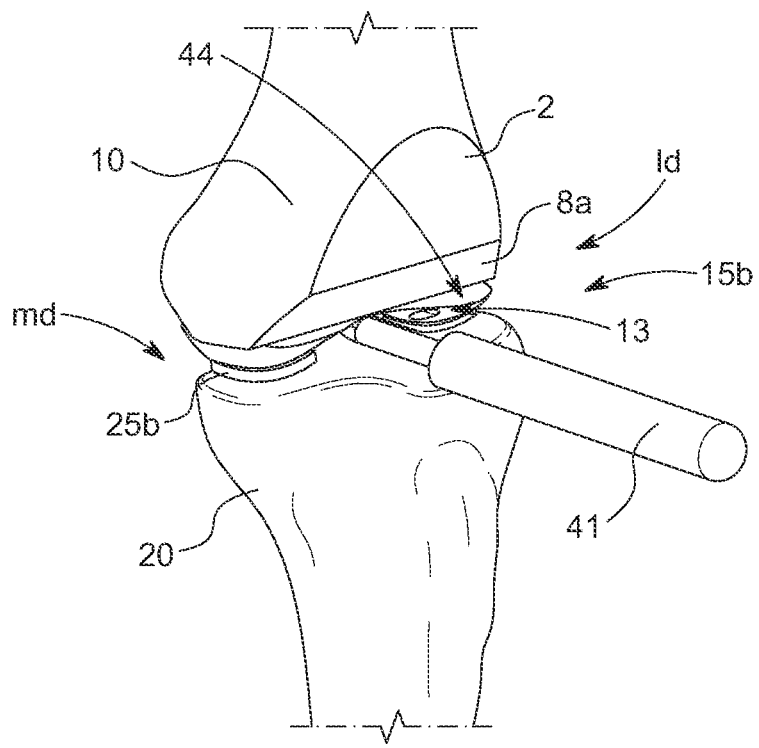
FIG. 12B is a perspective view depicting the distal referencing guide inserted into the gap.
Figure 13A:
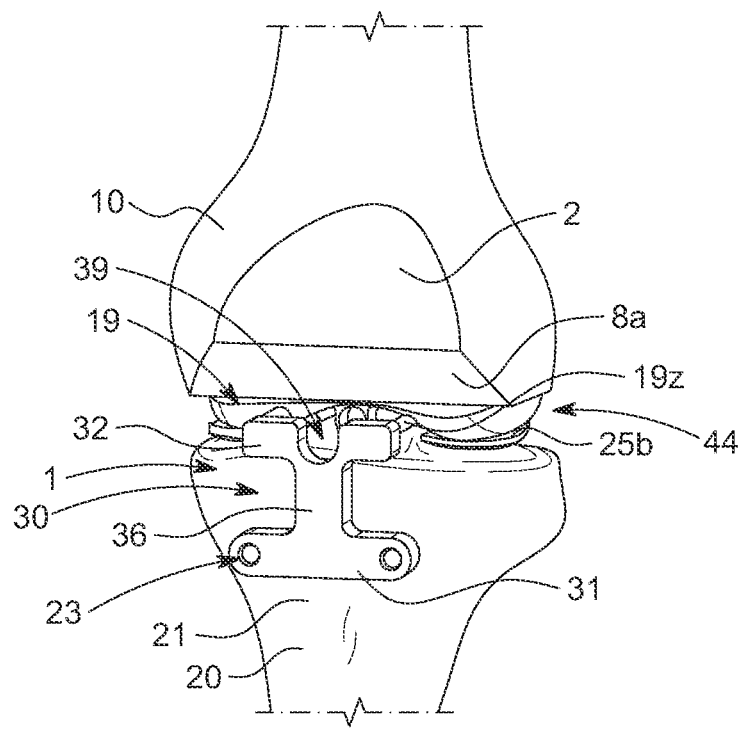
FIG. 13A is a perspective view showing the elements of FIG. 12C and further comprises an exemplary linking drill guide having orientation pins inserted into the condylar portions of the distal referencing guide.
Figure 13B:
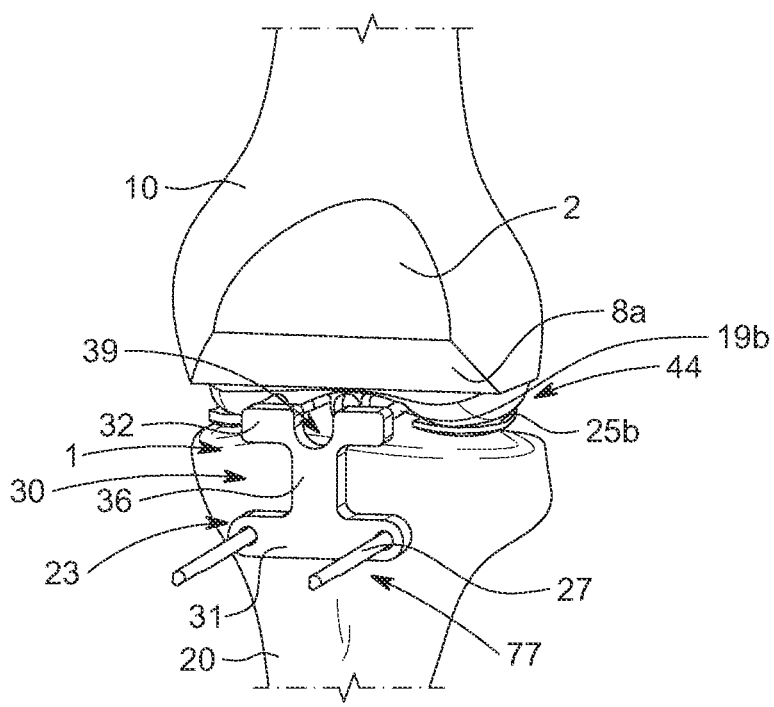
FIG. 13B is a perspective view of the elements shown in FIG. 13A and further depicts tibial linking pins having been inserted into the tibial reference holes in the linking drill guide.

As seen in FIG. 12A, the snap-on gap spacers 25b are affixed to the distal referencing portion 44 of the distal referencing guide 15b. The surgeon uses the modular handle 41 to insert the referencing portion 44 medially and laterally between the distal aspect of the resected femur 10 and the proximal aspect of the tibia 20 to fill the joint space 3 and determine the medial gap distance and (FIG. 12B) and the lateral gap distance Id (FIG. 13B). Unlike in the technique described above, a femoral trial 15a is not placed on the resected femur 10 during the linking transfer steps.

The distal referencing technique is carried out using a distal referencing guide 15b. An exemplary embodiment of an assembled distal referencing guide 15b is shown in FIG. 12A. The distal referencing guide 15b has a femoral referencing portion 44 having a medial partial condylar portion 45M and a lateral partial condylar portion 45L. Each condylar portion 45M, 45L has a complementary femoral engagement member 13. In the depicted exemplary embodiment, the complementary femoral engagement member 13 is a pin hole bore 13b formed anterior-to-posterior therethrough. Each pin hole bore 13b can be accessed anteriorly for use in orienting a linking drill guide 30, as indicated in FIG. 13A. A modular handle 41 is configured to readily attach and detach from the femoral referencing portion 44 for use in maneuvering the distal referencing guide 15b into and within the joint space 3. A distal portion of each of the condylar portions 45M, 45L is configured to receive a snap on spacer 25b. A plurality of thicknesses of snap on spacers 25b are provided. Appropriate thicknesses of snap on spacers 25b are selected such that the fully assembled distal referencing guide 15b matches the gap distance d determined in the prior step using the spoon gap spacers 25a (see FIG. 11).

Figure 12C:
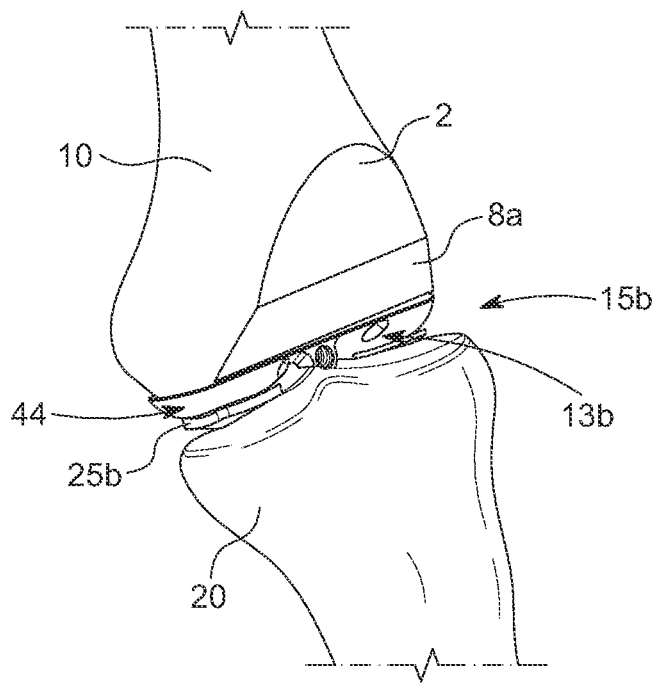
FIG. 12C is a perspective view of the distal referencing guide disposed within the gap, wherein the handle has been removed.

FIG. 12B shows use of the modular handle 41 to slide the distal referencing guide 15b into the joint space 3. As shown in FIG. 12C, the modular handle 41 can be removed from the distal referencing guide 15b after insertion, if desired.

As shown in FIG. 13A, with the distal referencing guide 15b in place in the joint space 3, a linking drill guide 30 is inserted into the incision. The depicted exemplary embodiment of the linking drill guide 30 has a recess 39 in the femoral portion 32 of the linking drill guide 30 to permit the modular handle 41 to be inserted through the recess 39 to engage the distal referencing portion 44 of the distal referencing guide 15b if desired. A pair of femoral engagement members 19, 19z in the form of orientation pins 19b are formed on or adjacent the femoral portion 32 of the linking drill guide 30. It will be appreciated that in other exemplary embodiments, femoral linking holes 22, 22z, or other femoral engagement members 19 may be used in lieu of or in addition to the orientation pins 19b depicted in FIG. 13A. The orientation pins 19b are inserted into the pin hole bores 13b in the condylar portions 45M, 45L until the tibial portion 31 of the linking drill guide 30 contacts the anterior tibial cortex 21. In this manner, the exemplary distally referencing linking drill guide assembly 1 is disposed in an engaged configuration. The linking drill guide 30 includes a pair of tibial reference holes 23, 23z on or adjacent the tibial portion 31 of the linking drill guide 30.

A modified embodiment of the linking drill guide 30 and associated assembly, systems, and methods described with reference to FIG. 13A is further contemplated. In such an embodiment, the orientation pins 19b of the linking drill guide 30 can be inserted directly into drill bores made in the distal femur 10. The exemplary linking drill guide 30 can be sized to have the orientation pins 19b extend into drill bore formed via a distal femoral resection guide (see 15c, FIG. 16). In certain exemplary embodiments, the orientation pins 19b can be spikes configured to engage the drill bores in the distal femur 10. In such exemplary embodiments, the spikes are the femoral engagement members 19 and the drill bores in the distal femur 10 are the complementary femoral engagement members 13.

Figure 13C:
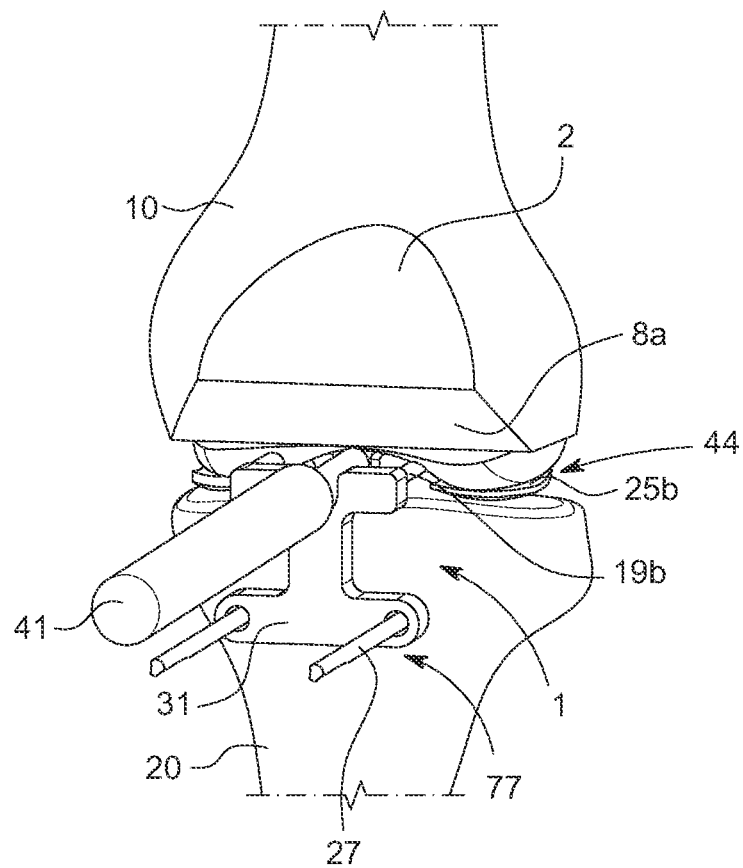
FIG. 13C is perspective view of the elements shown in FIG. 13B and further depicts the removable handle having been reattached to the femoral portion of the distal referencing guide.

As shown in FIG. 13B, tibial linking pins 27 are placed in each of the tibial reference holes 23, 23z in the linking drill guide 30. As shown in FIG. 13C, the modular handle 41 can optionally be used in this step for stability. The tibial linking pins 27 are inserted into the tibia 20. In certain embodiments, the tibial linking pins 27 are threaded at the leading end 11 (see FIG. 15).

Figure 14A:
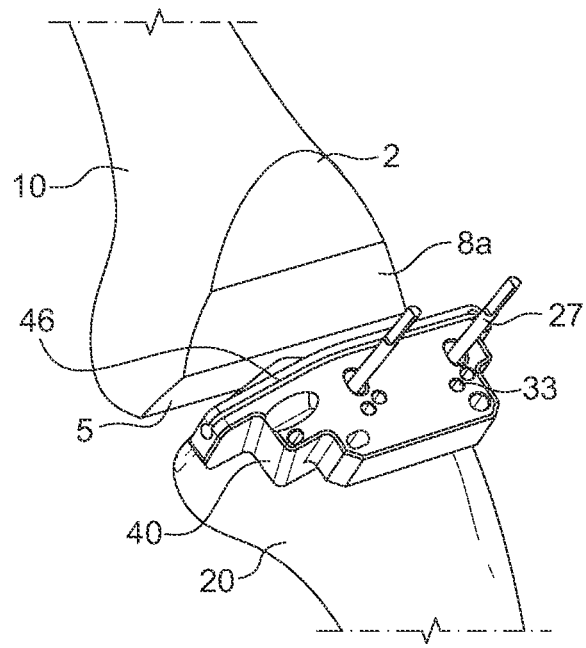
FIG. 14A is a perspective view showing a pivoting tibial resection disposed over the tibial linking pins remaining in tibia, wherein the distal gap spacer assembly and the linking drill guide have been removed.

As indicated in FIG. 14A, the linking drill guide 30 and the distal reference guide 15b is removed from the joint, leaving the tibial linking pins 27 in place in the proximal tibia 20. The receiving slots 87 of a pivoting tibial resection guide 40 are slid onto the tibial linking pins 27. From this point on, the technique is similar to the technique described above, except that a femoral trial 15a is not on the resected distal femur 10. It should be noted that once the linking pins 27 are placed into the tibia 20, there is no need to the femoral trial 15a to remain in place for any of the embodiments described herein.

Figure 14B:
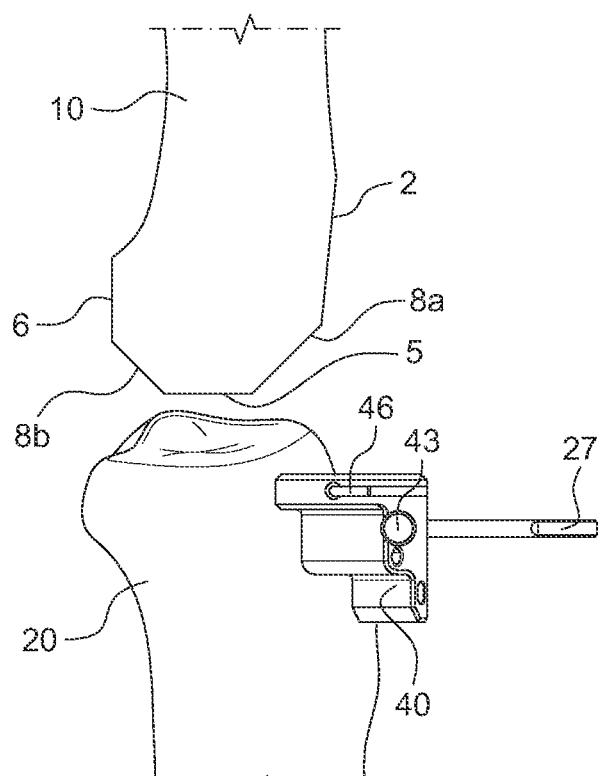
FIG. 14B is a side view of the elements shown in FIG. 14A.

As indicated in the side view of FIG. 14B, the instruments can be sized such that the tibial resection level is set automatically to match a 10 mm tibial implant construct (i.e., a tibial trial base 93 plus a meniscal trial insert 95). In embodiments, the linking drill guide 30 can be made to allow for other resection levels as needed or desired by the surgeon, such as by a plurality of linking guides, multiple pin holes, or an adjustable guide.

Figure 14C:
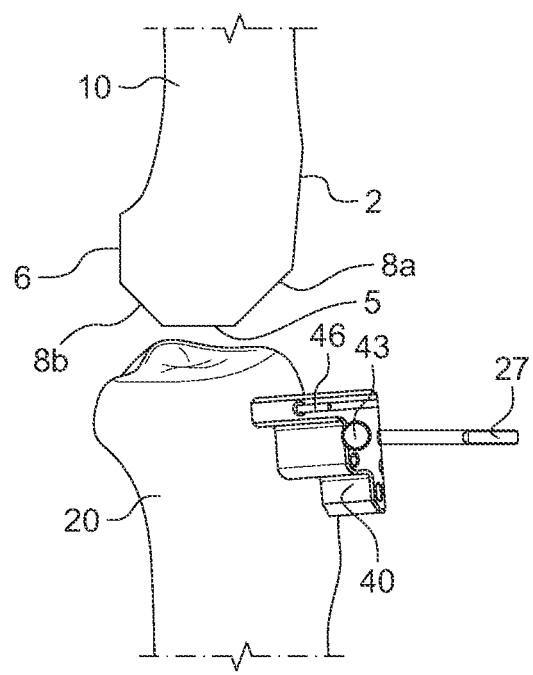
FIG. 14C is a side view of the elements depicted in FIG. 14B in which the tibial posterior slope of the tibial resection guide has been adjusted to match the natural slope of the patient's tibia.

As shown in FIG. 14C and with reference to FIG. 8, the tibial posterior slope PS can be adjusted as needed to match the natural anatomy, in the manner described above. The pivoting tibial resection guide 40 is configured such that the pivoting tibial resection guide 40 can be adjusted relative to the placement of the tibial linking pins 27. In embodiments, the pivoting tibial resection guide 40 can have a posterior slope angle θ in the range of about minus 3 degrees to about plus 10 degrees relative to the linking pins 27. Once the posterior slope angle θ is set, the pivoting tibial resection guide 40 can be locked at the selected posterior slope angle θ.

As described above with reference FIG. 9, the pivoting tibial resection guide 40 is pinned in place through the standard pin holes 33. A divergent fixation pin 34 can be used if desired for added stability. The tibial linking pins 27 are removed.

Figure 15:
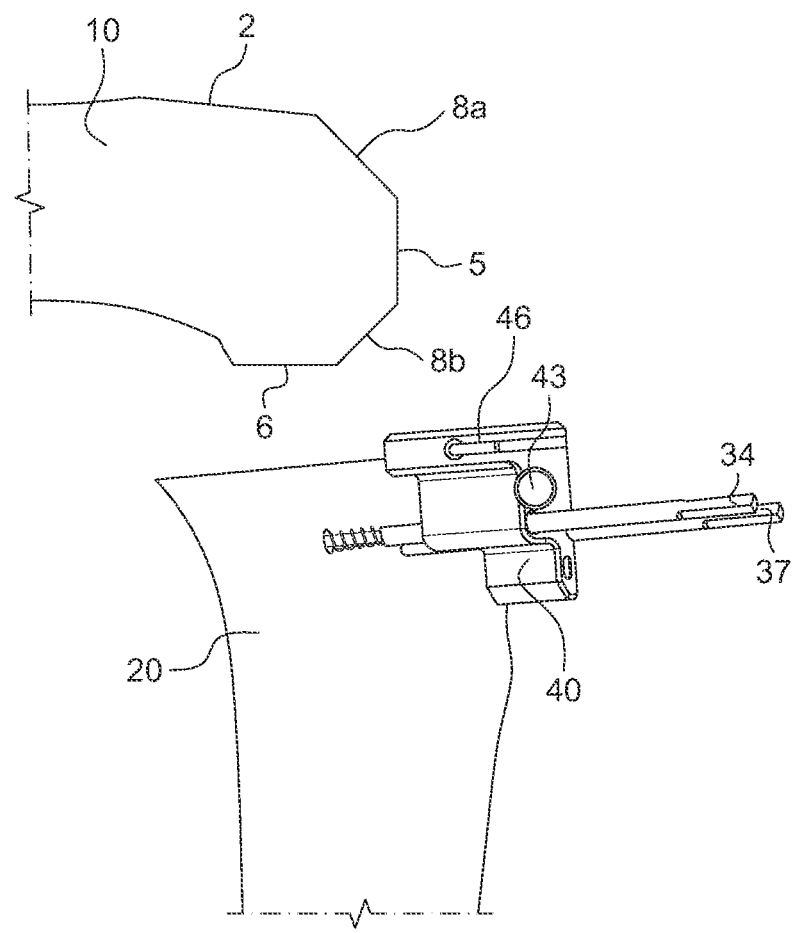

As shown in FIG. 15, a proximal tibial resection is performed through the resection slot 46 in the pivoting tibial resection guide 40. Unlike in the technique described above, there is no femoral trial 15a to remove prior to carrying out the tibial resection.

Once the tibial resection is complete, the surgeon selects an appropriate size tibial base and tibial insert trials. A femoral trial 15a is placed on the previously resected distal femur 10. If the distal referencing technique as described herein is used, the femoral trial 15a may not have a complementary femoral engagement member 13 such as the complementary femoral engagement member 13 disclosed in FIGS. 1-9. A trial reduction is carried out (see FIG. 29). The femoral sulcus, peg prep, and tibial keel prep can be performed according to the kinematic alignment technique or surgeon preference.

Distal Femoral Resection Guide Referencing Technique

FIGS. 16-28 generally depict method steps and exemplary devices and assemblies that include other embodiments of exemplary linking drill guide 30 and that can involve the use of a distal femoral resection guide 15c.

Figure 16:
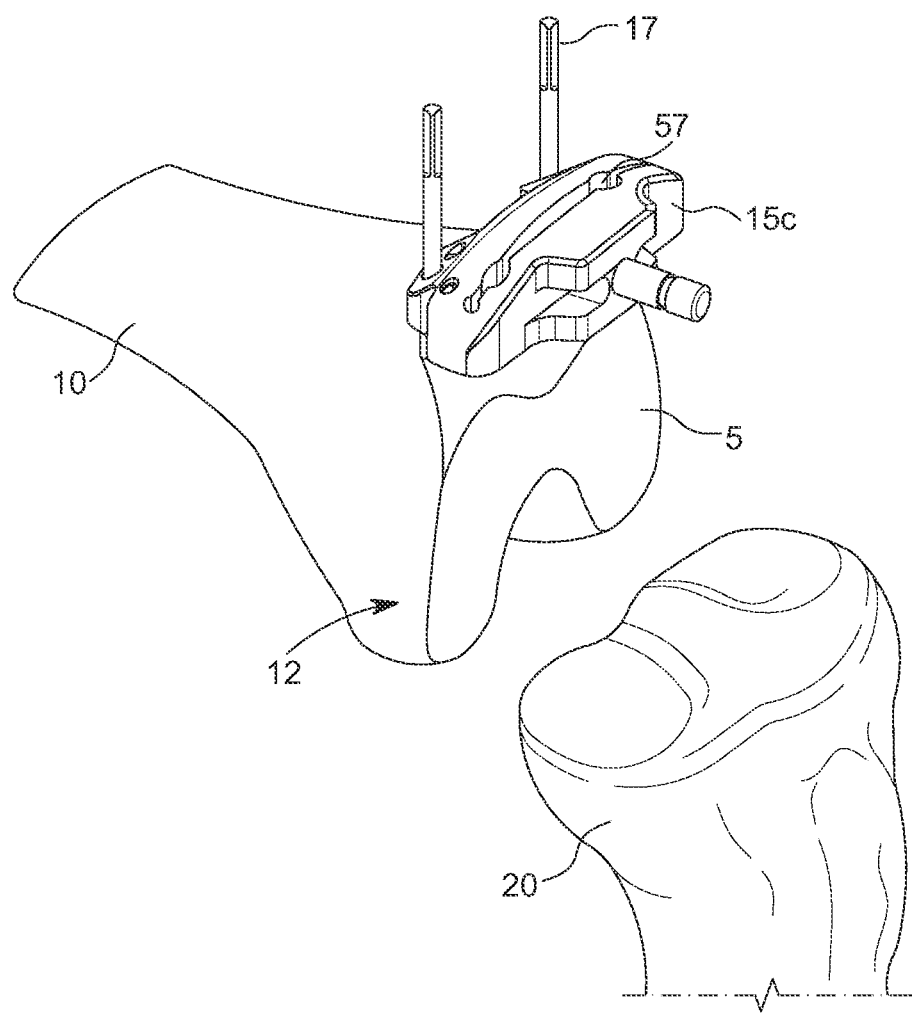

FIG. 16 is a perspective view of a knee in flexion. In the embodiments depicted in these figures, the femoral referencing instrument 15 is a distal femoral resection guide 15c. The distal femoral resection guide 15c has been slid over femoral linking pins 17 extending into the femur 10. In this embodiment, the femoral linking pins 27 are the standard pins that are otherwise used to locate the femoral distal cut guide. The distal femoral resection guide 15c was placed using kinematic alignment techniques known to surgeons. For example, the distal femoral resection guide assembly disclosed in U.S. Pat. App. Pub. No. 2019/0231365A1 may have been used to orient the distal femoral resection guide 15c. Once oriented, the surgeon locks the distal femoral resection guide's position and orientation relative to the distal femur 10 using the femoral linking pins 17. The surgeon then inserts a surgical saw through the resection slot 57 to resect the distal aspect of the femur 10 to create the distal resected surface 5 via the distal cut.

Figure 17A:
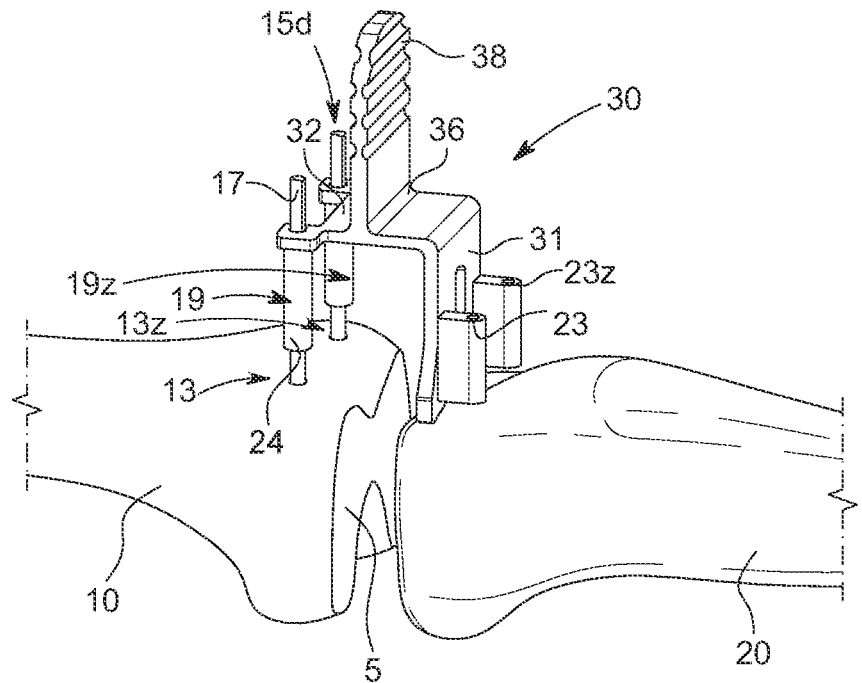
FIG. 17A is a perspective view of the knee is extension, wherein an exemplary embodiment of a linking drill guide is provided, wherein the exemplary linking drill guide is configured to be engaged to the pins previously used to secure the distal femoral resection guide in a resection orientation.

With the exemplary linking drill guide 30 depicted in FIG. 17A, the distal femoral resection guide 15c is then removed and the leg is placed in extension. It will be appreciated that the exemplary embodiment of the linking drill guide 30 used can influence which instrument serves as the femoral referencing instrument 15. For example, in FIG. 17A, the femoral resection guide 15c has been removed and the femoral linking pins 17, 15d remain disposed in the femur 10. Because the femoral linking pins 17 together with the depicted embodiment of the linking drill guide 30 can be used to mechanically transfer information about the orientation of the distal resected surface 5 of the femur 10 to the tibial resection guide 40, the femoral linking pins 17 in the depicted embodiment serve as a type of femoral referencing instrument 15. Similarly, in FIG. 17B, wherein the slot 57 of the distal femoral resection guide 15c, when engaged to the blade 19c of the exemplary linking drill guide 30, mechanically transfers information about the orientation of the orientation of the distal resected surface 5 of the femur 10 to the tibial resection guide 40, the distal femoral resection guide 15c is a type of femoral referencing instrument 15.

The exemplary linking drill guide 30 shown in FIG. 17A comprises a femoral portion 32. The femoral portion 32 comprises tubes 24 that can receive first and second femoral engagement members 19, 19z in the form of femoral linking pins 17. That is, the tubes 24 define linking holes 22 (see FIG. 5A). The tubes 24 and linking holes 22 can receive the femoral linking pins 17 in much the same manner as described above with reference to FIGS. 4 and 5A. In this manner, the depicted embodiment is configured to engage a first and a second femoral engagement member 19, 19z. In the depicted embodiment, the first and second complementary femoral engagement members 13, 13z are drill bores made directly into the distal femur 10. In FIG. 17A, the femoral linking pins 17 also serve as the first and second femoral engagement members 19, 19z. The distal femoral resection guide 15c has been removed and the placement of the femoral linking pins 17 in the distal aspect of the femur 10 retain the information about the plane of distal resection, which is coplanar with the distal resected surface 5. That is, an imaginary shortest possible line connecting the two femoral linking pins 17 can function as a reference line that is parallel to the plane of distal resection of the femur 10.

The exemplary linking drill guide 30 further comprises a tibial portion 31 having tubes 24 defining tibial reference holes 23, 23z, and a body 36 connecting the femoral portion 32 to the tibial portion 31. A handle 38 may optionally be provided to facilitate installation and removal of the linking drill guide 30. The handle 38 may be removable, or the handle 38 may be a permanent and integral part of the linking drill guide 30. The body 36 of the linking drill guide 30 transfers the information regarding the orientation of the plane of distal resection (which is coplanar with the distal resected surface 5) to the tibial portion 31 of the linking drill guide 30.

Figure 18:
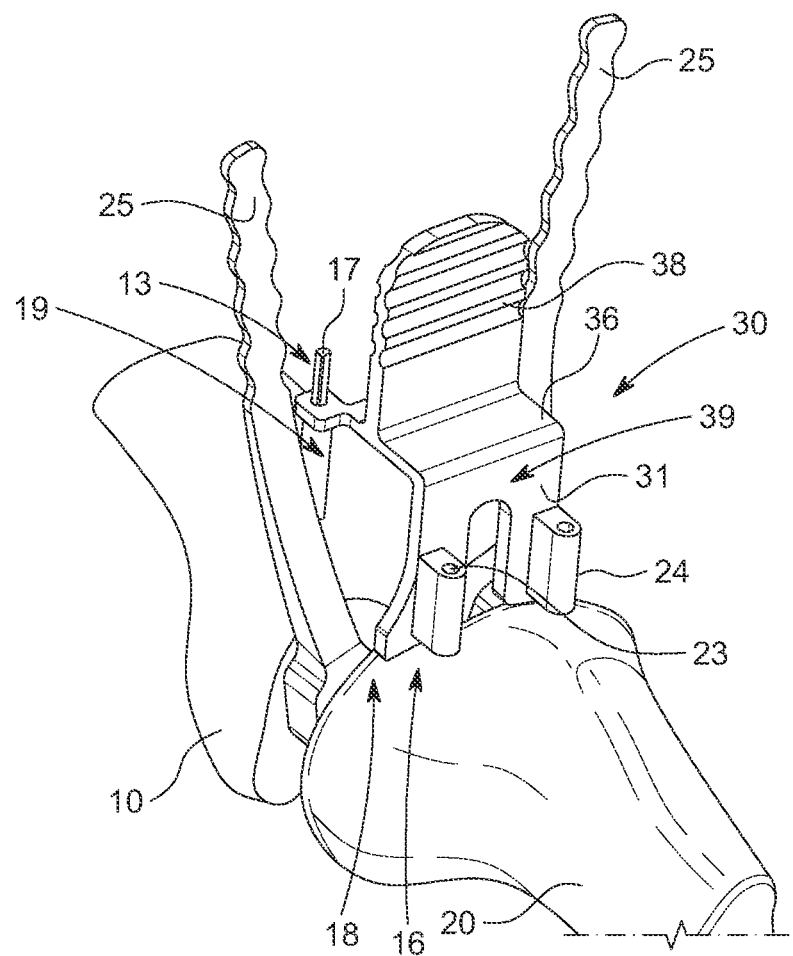
Figure 19A:
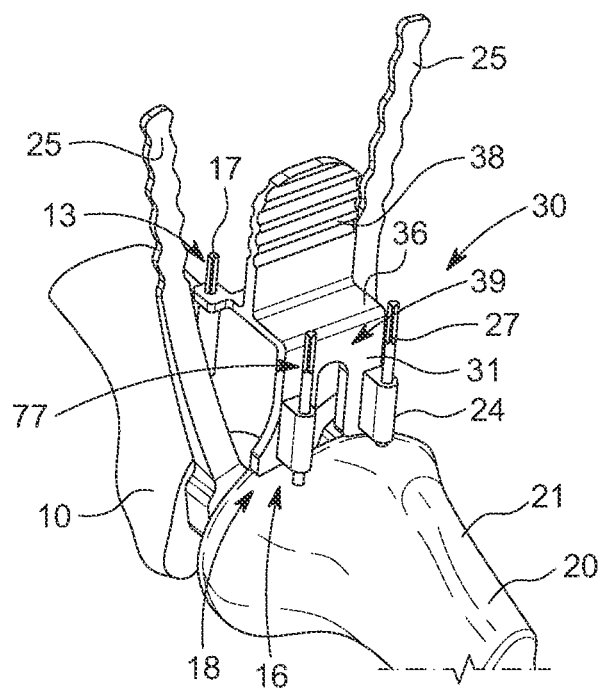
FIG. 19A is a perspective view of the elements depicted in FIG. 18 and further comprises tibial linking pins extending into the tibia through the tibial portion of the linking drill guide.
Figure 19B:
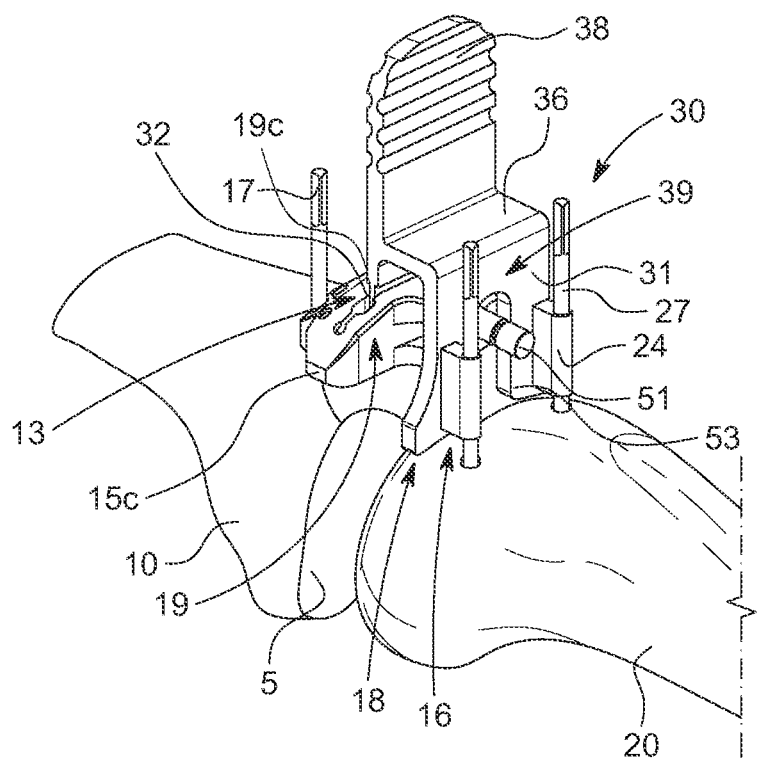
FIG. 19B is a perspective view of the elements depicted in FIG. 17B and further comprises tibial linking pins extending into the tibia through the tibial portion of the linking drill guide.

As better seen in FIGS. 18, 19A, and 19B, the distal end 16 of the tubes 24 define the tibial reference holes 23, 23z. The distal end 16 of each of the tubes 24 is preferably recessed from the posterior distal end 18 of the tibial portion 31 of the linking drill guide 30. The inferior surface 53 (FIG. 19B) of the tibial portion 31 aligns with the tibial resection plane when the linking drill guide 30 is in the engaged configuration. This feature permits the surgeon to visualize the tibial resection cut before it is made. The recess 39 further permits direct marking of the tibia 20 by creating a line connecting the two opposing inferior surfaces 53 at the distal end 18 of the tibial portion 31. Direct marking is commonly performed with surgical grade single use marker or through a cautery device. Depending upon preference, a line drawn through the recess 39 separating the opposing inferior surfaces 53 at the distal end 18 of the tibial portion 31 may be made.

FIG. 18 further shows spreading devices 49 such as gap spacers 25 inserted into the joint gap 3 to ascertain and verify the medial and lateral distance between the resected distal condyles of the femur 10 and the medial and lateral condyles of the adjacent proximate tibial plateau 20 of the same leg. Lamina spreaders or other tensioning devices may be used to apply tension to the joint in place of the distal referencing gap spacers 25. Once determined, the surgeon inserts the tibial linking pins 27 as depicted in FIG. 19A.

Figure 20A:
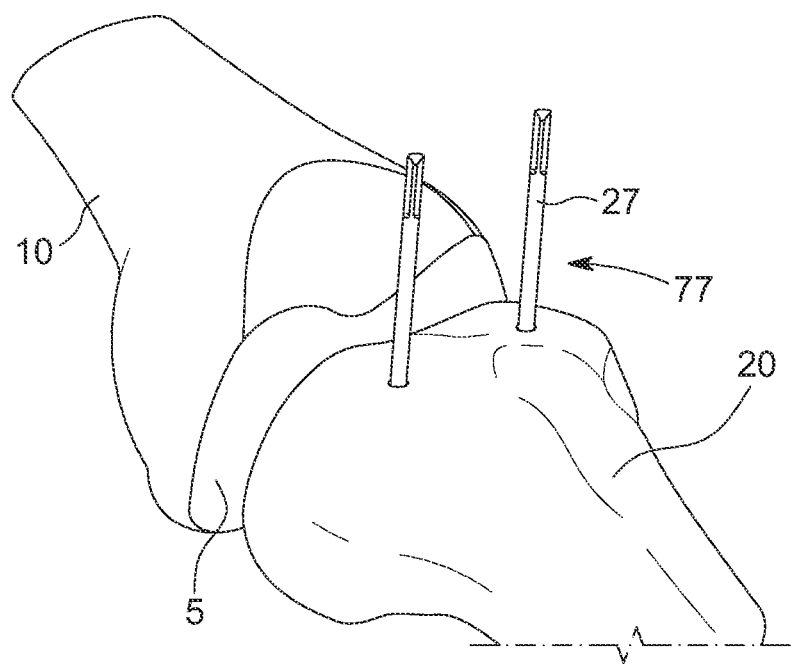
FIG. 20A is a perspective view of the tibial linking pins remaining in the tibia after all other elements have been removed.
Figure 21A:
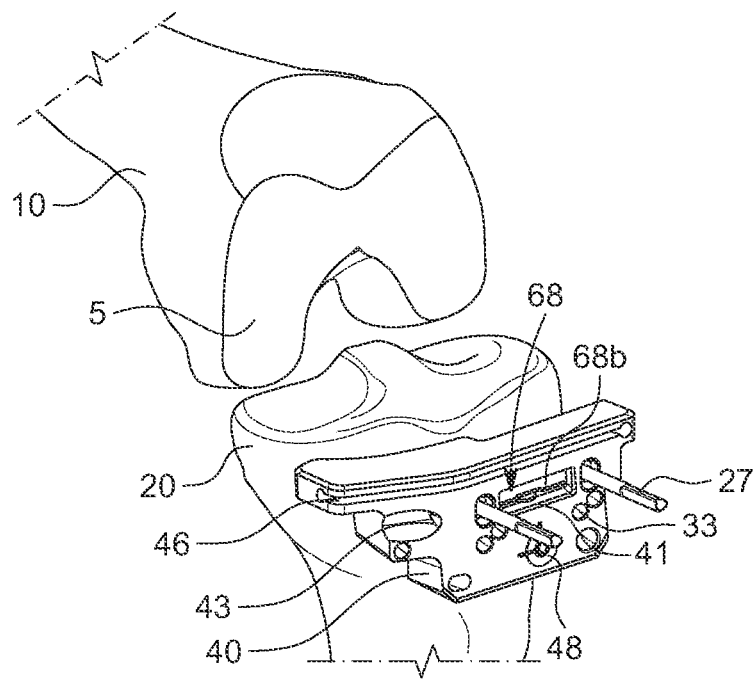
FIG. 21A is a perspective view of a pivoting tibial resection guide disposed upon the tibial linking pins depicted in FIG. 20A.
Figure 22:
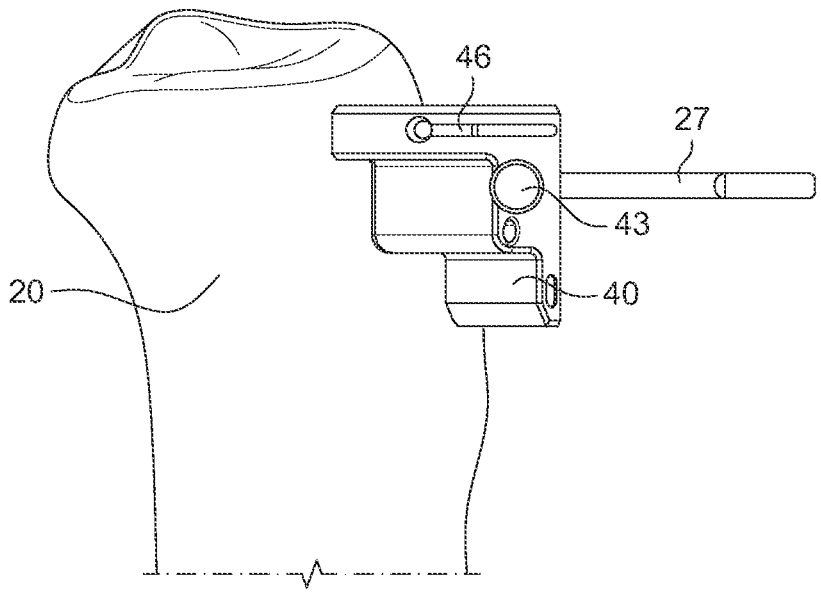

FIG. 20A shows the tibial linking pins 27 remaining disposed in the proximal aspect of the anterior cortex 21 of the tibia 20 after the linking drill guide 30 has been removed. As seen in FIGS. 21A and 22, the receiving slots 87 of a pivoting tibial resection guide 40 can then be slid over the remaining tibial linking pins 27. The locking mechanism 48 is in an unlocked position. The anterior face of the locking mechanism 48 can be provided with a visual indicator to let the surgeon know which position the locking mechanism 48 is in. In the depicted embodiment, the indicator disposed at the 9 o'clock position indicates that the locking mechanism 48 is unlocked. The posterior slope PS (see FIG. 8) can then be adjusted and the proximal aspect of the tibia 20 can be resected as described above (see also generally FIGS. 23-28).

Figure 17B:
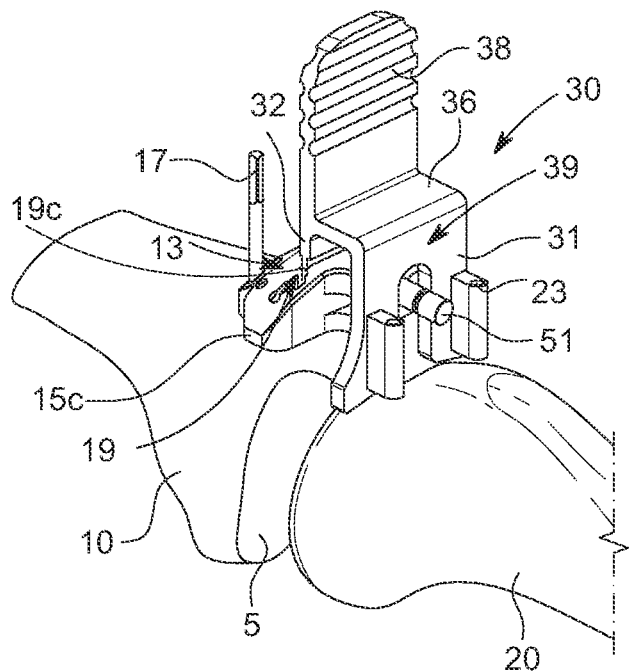
FIG. 17B is a perspective view of a knee in extension, wherein another exemplary embodiment of a linking drill guide comprising a blade configured to fit securely into the femoral resection slot of the distal femoral resection guide is provided.

Referring to FIG. 17B, another exemplary embodiment of a linking drill guide 30 is provided. In the depicted embodiment of the associated distally referencing linking drill guide assembly 1, the distal femoral resection guide 15c can be viewed as serving as the femoral referencing instrument 15. The femoral resection slot 57 also functions as the first complementary femoral engagement member 13 of the femoral referencing instrument 15. The first femoral engagement member 19 on the femoral portion 32 of the linking drill guide 30 is a blade 19c that is dimensioned to fit closely into the femoral resection slot 57. In the depicted embodiment, a recess 39 may be present in the tibial portion 31 of the linking drill guide 30. The recess 39 permits the linking drill guide 30 to be slid over a stem portion 51 of the distal femoral resection guide 15c.

The blade 19c of the linking drill guide 30 is slid into the femoral resection slot 57 of the distal femoral resection guide 15c with the leg in extension. FIG. 19B shows the tibial linking pins 27 having been inserted into the tibial reference holes 23. It is then possible to proceed as outlined in FIGS. 21A and 22 and as described above.

Figure 20B:
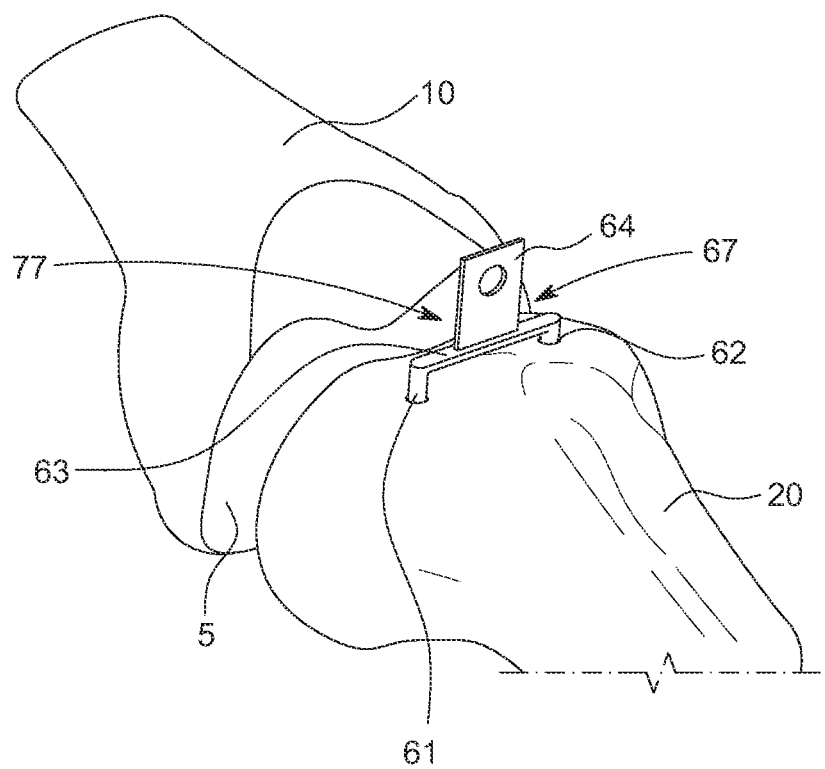
FIG. 20B is a perspective view of an exemplary spike plate remaining in the bores left by the tibial linking pins after the tibial linking pins and all other elements have been removed.

FIG. 20B shows a spike plate 67 being used as a reference instrument for the pivoting tibial resection guide 40 instead of tibial linking pins 27. As shown in FIGS. 19A and 19B, the tibial linking pins 27 are inserted through the tibial reference holes 23, 23z in the tibial portion 31 of the linking drill guide 30 and are drilled into the anterior cortex 21 of the proximal tibia 20. In FIG. 20B, both the linking drill guide 30 and the tibial linking pins 27 have been removed, thereby leaving the drill bores in the anterior cortex 21 of the proximal tibia 20. A spike plate 67 comprising a first spike member 61 and second spike member 62 connected by a body portion 63 and having a linking tab 64 to facilitate selective engagement to the pivoting tibial resection guide 40 is provided. As discussed further below, the linking tab 64 can be representative of the orientation of the plane otherwise formed by the compound axes of the tibial linking pins 27. The first and second spoke members 61, 62 of the spike plate 67 are inserted into the tibial drill bore holes left by the linking tibial pins 27.

In certain exemplary embodiments, the spike plate 67 may be a single use, disposable item. In other exemplary embodiments, the spike plate may be made from stainless steel or any other clinically proven biocompatible material of sufficient strength and durability.

Figure 21B:
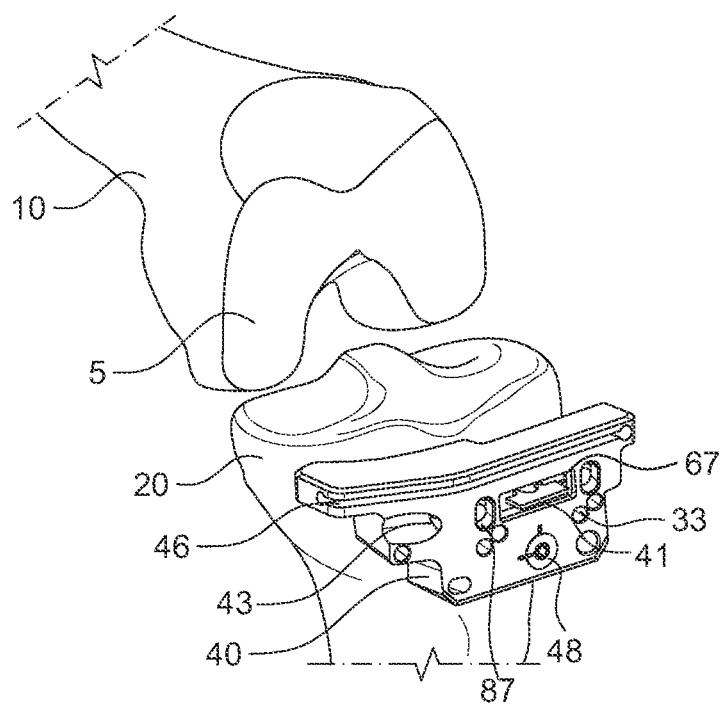
FIG. 21B is a perspective view of a pivoting tibial resection guide disposed upon a linking tab of the spike plate depicted in FIG. 20B.

As seen in FIG. 21B, a pivoting tibial resection guide 40 having a reference slot 41 is slid over the linking tab 64 of the spike plate 67. The linking tab 64 is visible through the open resection slot 41. The linking tab 64 is oriented parallel to the resection slot 46 and is thereby indicative of the orientation of the plane otherwise formed by the compound axes of the tibial linking pins 27 (see PS, FIG. 8). The linking tab 64 may optionally be provided with a visual indicator such as a different color from the surrounding instrumentation to better facilitate the surgeon's previsualization of the tibial resection cut, which is made on a parallel plane above the plane otherwise formed by the compound axes of the tibial linking pins 27. The surgeon can lock the linking tab 64 to the reference slot 41 using the locking mechanism 48 on the anterior end of the pivoting tibial resection guide 40. In FIG. 21B, the locking mechanism 48 is shown in the unlocked position.

The spike plate 67 permits medial and lateral positioning of the pivoting tibial resection guide 40 as well as internal and external rotation of the pivoting tibial resection guide 40, whereas the use of the tibial linking pins 27 precludes medial and lateral positioning of the pivoting tibial resection guide 40.

Figure 23:
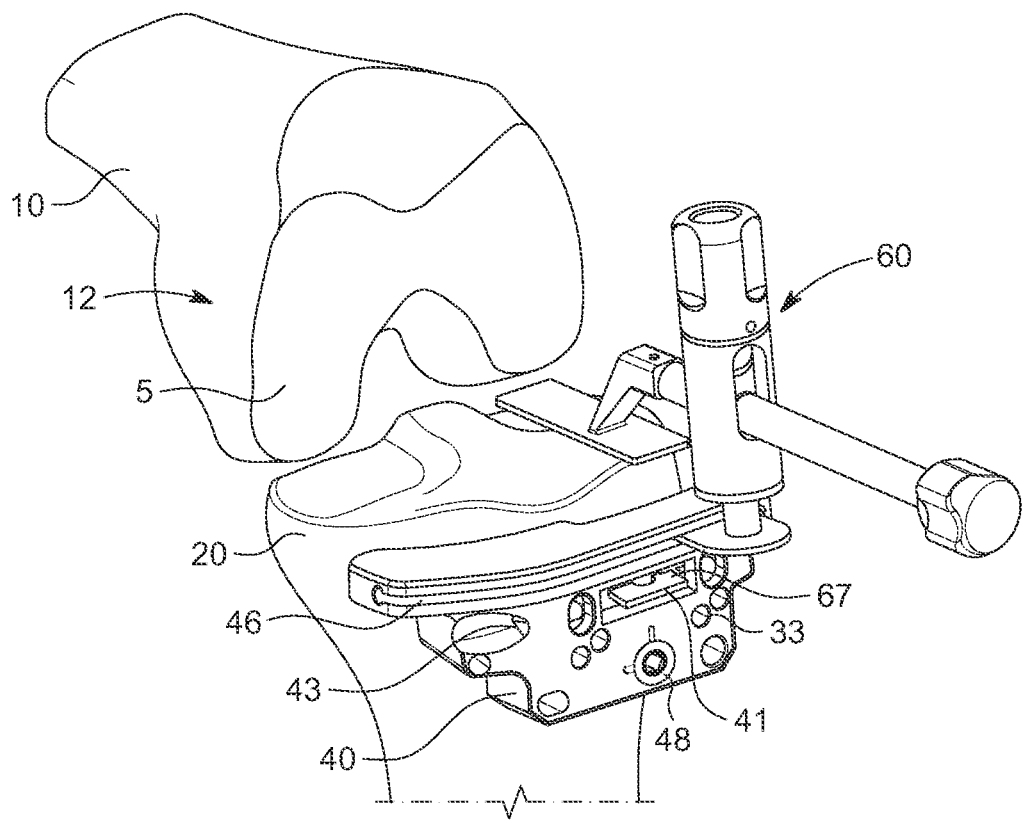
Figure 24:
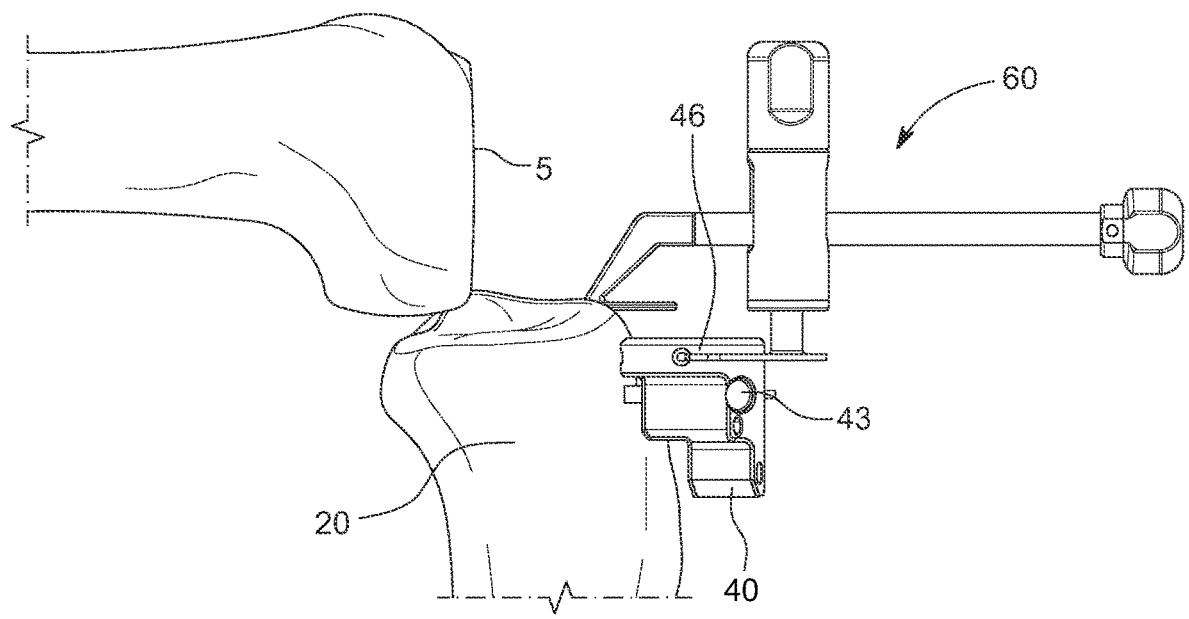
Figure 25:
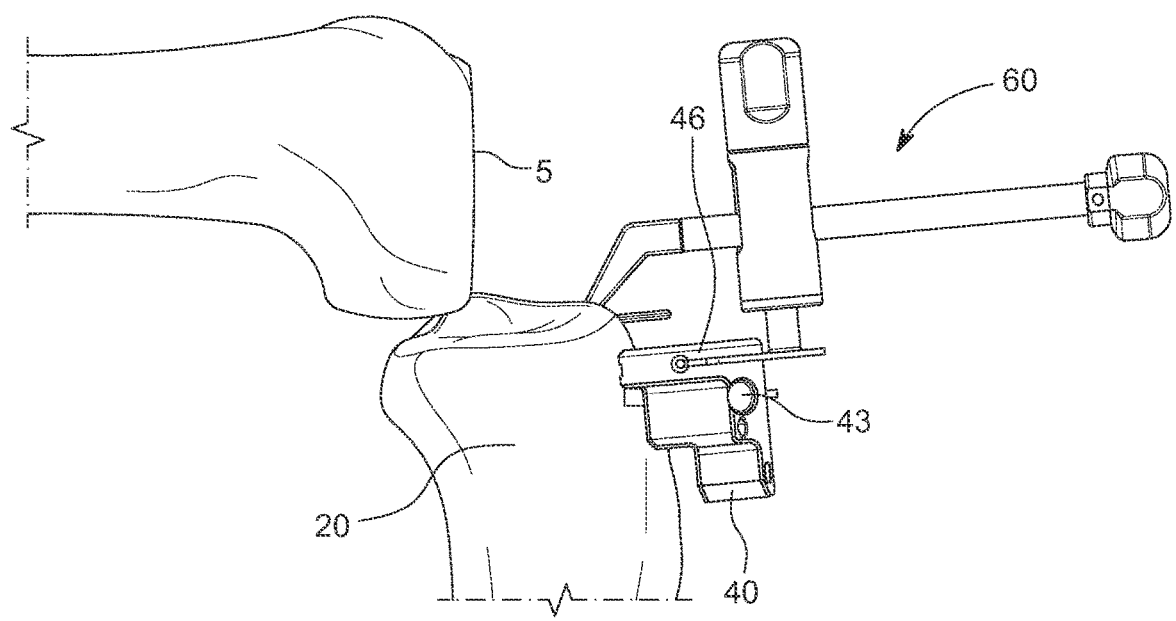

FIGS. 23-25 depict a tibial visual slope gage 60 that may be optionally placed into the resection slot 47 of the pivoting tibial resection guide 40. The posterior slope angle θ of the tibial resection guide 40 can be adjusted from about −3° to about +10° relative to the placement of the tibial linking pins 27, or relative to the spike plate 67 placement in embodiments involving the use of the spike plate 67. Once the desired slope and orientation is achieved, the pivoting action may be locked by rotating the locking mechanism 48.

The locking mechanism 48 depicted in FIG. 21B and in the cross-sectional view of FIG. 30 is in an unlocked position. The locking mechanism 48 may be a friction locking mechanism such as the one depicted in FIG. 30, but other locking mechanism configured to selectively fix the orientation of the pivoting tibial resection guide 40 are considered to be within the scope of this disclosure. For example, a mechanical locking mechanism 48 may be provided in certain exemplary embodiments.

Figure 27:
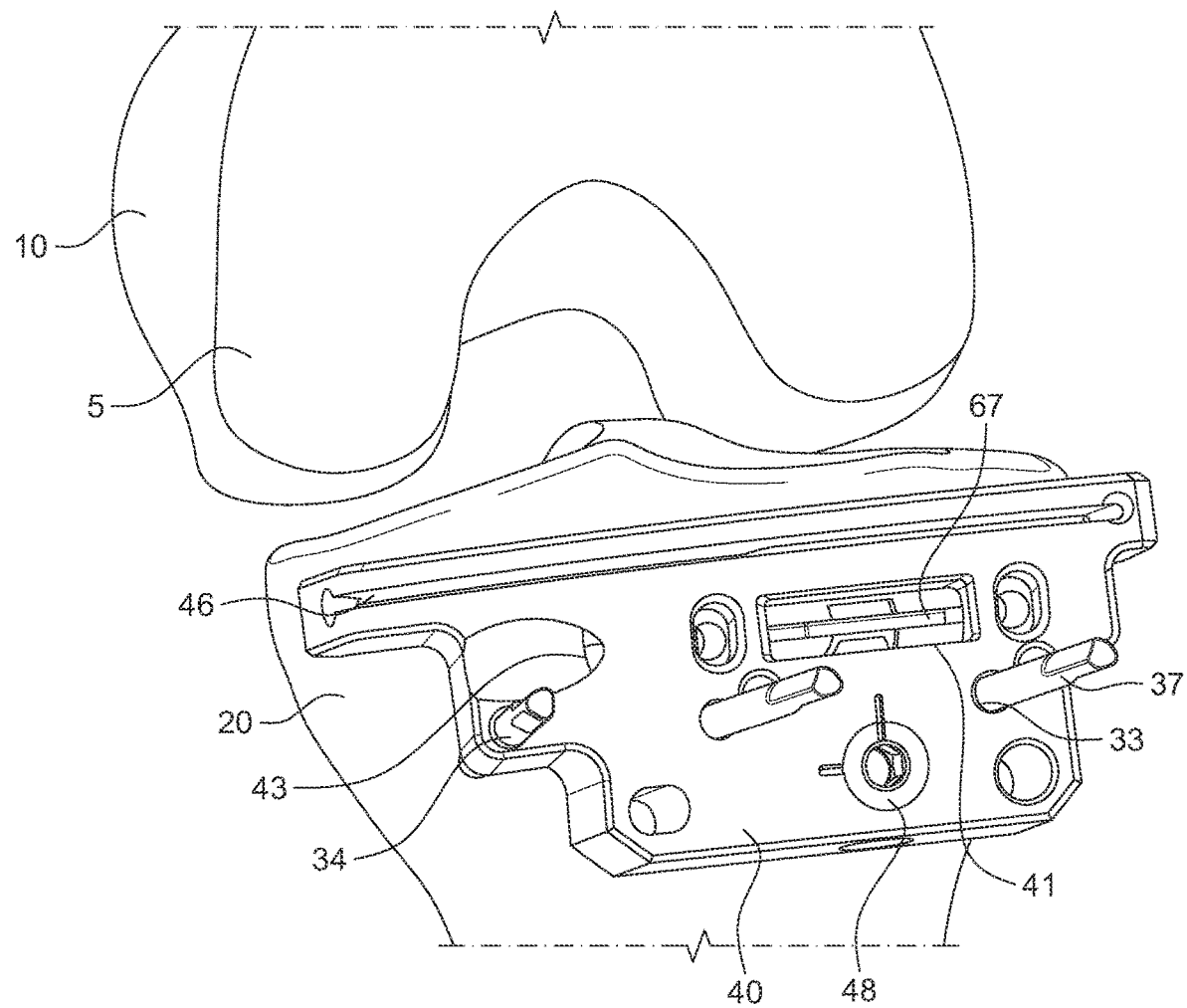

With reference to the locking mechanism of FIG. 30 and with further reference to FIG. 27, a surgeon or technician can lock the locking mechanism by inserting a keyed instrument through the interface of the locking mechanism 48. The keyed instrument may be a screwdriver, hex key, or other keyed instrument having a keyed end of any shape that is dimensioned to closely engage a complementary key shape in an interface that communicates rotationally with the cam 73. Upon rotating the keyed instrument, the interface rotates the cam 73 in the same direction. The cam 73 translates the rotational force to linear force by pushing the cam follower 74 against the springs 75. The springs 75 in turn transfer the linear force to the shaft 71 and the shaft 71 in turn transfers the linear force as friction to the pivoting guide 66. The application of this friction thereby prevents the pivoting assembly 55 from rotating axially. In this manner, the surgeon or technician can be said to "lock" the pivoting tibial resection guide at the desired posterior slope angle θ.

It will be understood that in embodiments comprising tibial linking pins 27, the tibial linking pins 27 extend through the tibial engagement holes 68a of the pivoting guide 66 to selectively engage the pivoting tibial resection guide 40 to the tibia 20. The tibial engagement holes 68a generally align with the receiving slots 87 of the pivoting tibial resection guide 40. Likewise, in embodiments that include a linking tab 64, the slot 68b of the pivoting guide 66 is desirably dimensioned to receive the linking tab 64 of the spike plate 67.

Figure 26:
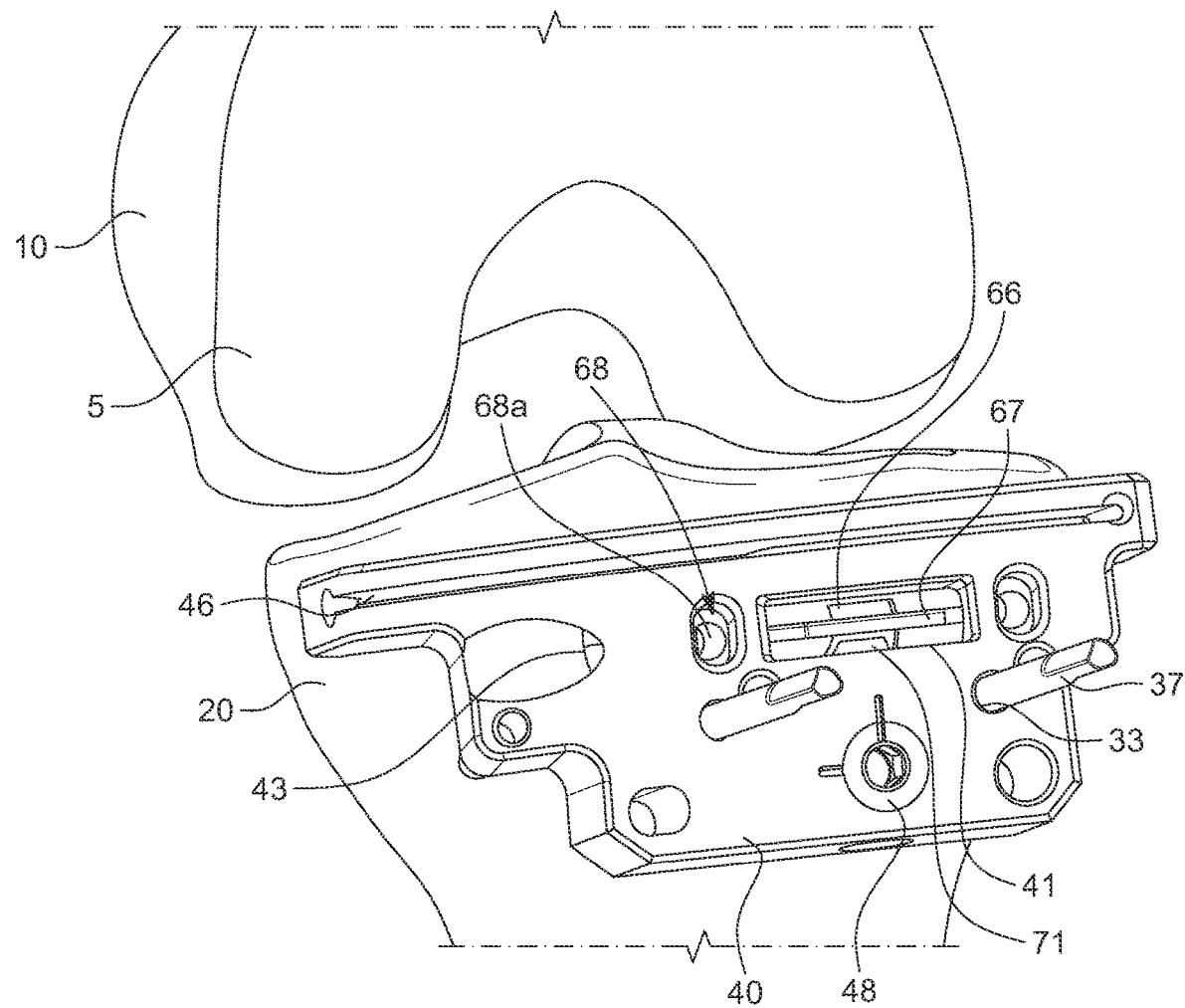

As shown in FIG. 26, the slope gage is removed after the slope of the pivoting tibial resection guide 40 is set. Standard pins 37 are then placed through the standard pin holes 33 in the pivoting tibial resection guide 40. The pivoting tibial resection guide 40 may be moved from the standard holes to the +2 mm location if desired. The locking mechanism 48 is shown in the locked position. In the depicted embodiment, the visual indicator in the 12 o'clock position indicates that the locking mechanism 48 is locked. Other visual indicators that indicate the position of the locking mechanism are considered to be within the scope of this disclosure.

FIG. 27 shows the pivoting tibial resection guide 40 disposed at the desired posterior slope PS (see FIG. 8) and further depicts a divergent fixation pin 34 extending through the pivoting tibial resection guide 40 to further secure the pivoting tibial resection guide 40 to the tibia 20 at the desired slope. The resection slot 46 in the pivoting tibial resection guide 40 orients the resection plane of the proximal end 29 of the proximal tibia 20.

Figure 28:
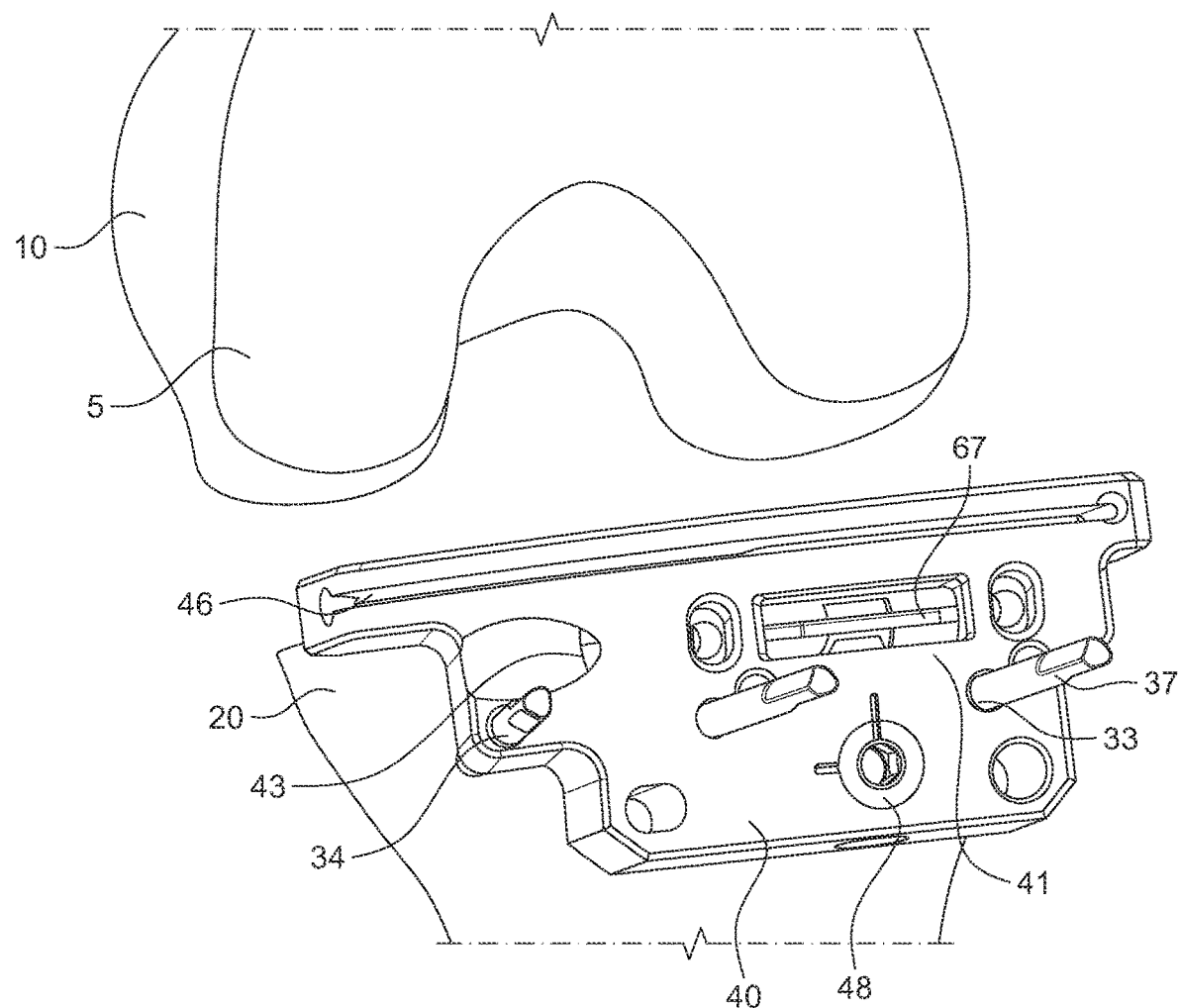

FIG. 28 depicts the pivoting tibial resection guide 40 disposed at the desired posterior slope PS (see FIG. 8), wherein the proximal end 29 (FIG. 27) of the proximal tibia 20 has been resected.

FIG. 29 is a perspective view of a femoral trial 15a, tibial trial base 93 and meniscal trial insert 95 that have been selected based on sizing criteria. Without being bound by theory, it is contemplated that the exemplary distally referencing linking drill guides 30 and/or the exemplary distally referencing linking drill guide assemblies 1 described herein can directly link the orientation of the distal cut (which results in the distal resected surface 5 of the distal femur 10) to the orientation of the proximal cut of the proximal tibia 20 to thereby reduce the possibility for surgeon error significantly while further eliminating one or more extra steps otherwise required by prior independently referencing or indirectly linking kinematic alignment techniques. The minimal size of the exemplary distally referencing linking drill guides 30 and the exemplary distally referencing linking drill guide assemblies 1 allows the linking drill guide 30 and drill guide assembly 1 to fit in the operative area without the need for additional instrumentation that extends significantly outside of the incision. It is contemplated that the minimal amount of instrumentation may facilitate instrument re-sterilization between procedures.

The instruments can be provided in the form of a kit. The components of the kit are preferably arranged in a convenient format, such as in a surgical tray or case. However, the kit components do not have to be packaged or delivered together, provided that they are assembled or collected together in the operating room for use at the time of surgery. An exemplary kit can include any suitable embodiment of a linking drill guide 30, variations of the linking drill guide 30 described herein, and any other linking drill guides 30 according to an embodiment. While it is contemplated that an exemplary kit may further include one or more femoral engagement members 19, 19z, etc. one or more tibial engagement members 77, 77z, etc., and one or more femoral referencing instruments 15, it will be appreciated that certain kits may lack some or all of these elements. Any suitable embodiment of a femoral engagement members 19, variations of the femoral engagement members 19 described herein, and any other femoral engagement members 19 according to an embodiment are considered to be within the scope of this disclosure. Any suitable embodiment of a tibial engagement members 77, variations of the tibial engagement members 77 described herein, and any other tibial engagement members 77 according to an embodiment are considered to be within the scope of this disclosure. Any suitable embodiment of a femoral referencing instrument 15, variations of the femoral referencing instruments 15 described herein, and any other femoral referencing instrument 15 according to an embodiment are considered to be within the scope of this disclosure.

Selection of a suitable number or type of linking drill guide 30, femoral engagement member 19, tibial engagement member 77, and femoral referencing instruments 15, to include in a kit according to a particular embodiment can be based on various considerations, such as the procedure intended to be performed using the components included in the kit.

An exemplary medical device can comprise: a femoral portion, the femoral portion configured to engage a first femoral engagement member; a tibial portion, the tibial portion configured to engage a first tibial engagement member; and a body connecting the femoral portion to the tibial portion.

With such an exemplary medical device, the first femoral engagement member can be selected from the group consisting essentially of: a femoral linking pin, a blade, a slot, a lip, a clamp, a hook, a protrusion, a recesses, a spike, a magnet, an orientation pin, and combinations thereof.

With such an exemplary medical device, the first tibial engagement member can be selected from the group consisted essentially of: a hole, a slot, a recess, a protrusion, a clamp, a lip, a magnet, a spike, and combinations thereof.

An exemplary distally referencing linking drill guide assembly can comprise: a linking drill guide comprising: a femoral portion, the femoral portion configured to engage a first femoral engagement member, a tibial portion, the tibial portion configured to engage a first tibial engagement member, and a body connecting the femoral portion to the tibial portion; and a femoral referencing instrument, the femoral referencing instrument having a first complimentary femoral engagement member, the first complimentary femoral engagement member being configured to engage the first femoral engagement member, wherein the distally referencing linking drill guide assembly has an engaged configuration when the first femoral engagement member engages the first complimentary engagement member, and wherein the distally referencing linking drill guide assembly has a disengaged configuration when the first femoral engagement member does not engage the first complementary femoral engagement member.

Such an exemplary assembly may further comprise a spreading device configured to be disposed between a resected distal femur and a proximal tibia to ascertain a distance between the distal femur and the proximal tibia. The spreading device is selected from the group consisting essentially of a gap spacer, a lamina spreader, a ratcheting tensioner, or other knee ligament tensioning devices.

Such an exemplary assembly may have the femoral portion further configured to engage a second femoral engagement member and the femoral referencing instrument can further comprise a second complementary femoral engagement member, the second complementary femoral engagement member being configured to engage the second femoral engagement member. The second femoral engagement member can be configured to selectively engage the second complementary femoral engagement member.

Such an exemplary assembly may have a femoral referencing instrument that is selected from the group consisting essentially of: a femoral trial, a distal referencing guide, pins, and a femoral distal cut guide.

Such an exemplary assembly may have a tibial portion of the linking drill guide that is further configured to engage a second tibial engagement member.

Such an exemplary assembly may have an engaged configuration that comprises the first femoral engagement member directly engaging the first complimentary femoral engagement member.

Such an exemplary assembly may have an engaged configuration that comprises the first femoral engagement member indirectly engaging the first complimentary femoral engagement member.

Such an exemplary assembly may have a first femoral engagement member that is selected from the group consisting essentially of: a femoral linking pin, a blade, a slot, a lip, a clamp, a hook, a protrusion, a recesses, a spike, a magnet, an orientation pin, and combinations thereof.

Such an exemplary assembly may have a first tibial engagement member that is selected from the group consisted essentially of: a hole, a slot, a recess, a protrusion, a clamp, a lip, a magnet, a spike, and combinations thereof.

An exemplary medical device can comprise: a femoral portion, the femoral portion comprising a blade dimensioned to fit closely into a femoral resection slot of a distal femoral resection guide; a tibial portion, the tibial portion having tubes defining tibial reference holes; and a body connecting the femoral portion to the tibial portion.

Such an exemplary assembly may further comprise a handle engaged to the body.

Such an exemplary assembly may have tubes defining tibial reference holes that are recessed from a posterior distal end of the tibial portion of the linking drill guide.

Such an exemplary assembly may have an inferior surface of the tibial portion that aligns with a tibial resection plane when the linking drill guide is in the engaged configuration.

Another exemplary medical device can comprise: a femoral portion, the femoral portion comprising a first femoral engagement member; a tibial portion, the tibial portion configured to engage a first tibial engagement member; and a body connecting the femoral portion to the tibial portion.

Yet another medical device can comprise: a femoral portion, the femoral portion comprising a first femoral engagement member; a tibial portion, the tibial portion comprising a first tibial engagement member; and a body connecting the femoral portion to the tibial portion.

An exemplary method can comprise: engaging a femoral referencing instrument to a distal femur; engaging a first femoral engagement member directly or indirectly to the distal femur; and engaging a linking drill guide directly or indirectly to the first femoral engagement member, wherein the linking drill guide comprises: a femoral portion, the femoral portion configured to engage the first femoral engagement member, a tibial portion, the tibial portion configured to engage a first tibial engagement member, and a body connecting the femoral portion to the tibial portion.

In the exemplary method, the step of directly engaging the first femoral engagement member to the distal femur can comprise having the first femoral engagement member physically contact an anterior cortex of the distal femur.

In the exemplary method, the step of indirectly engaging the first femoral engagement member to the distal femur can comprise having the first femoral engagement member physically contact a first complementary engagement member on an intermediate femoral device, wherein a portion of the intermediate femoral device physically contacts the distal femur.

In the exemplary method, the step of indirectly engaging the first femoral engagement member to the distal femur can further comprise having the first femoral engagement member physically contact a first complementary engagement member on an intermediate device. A portion of the intermediate device can physically contact a subsequent intermediate device, and a portion of the subsequent intermediate device can physically contact the distal femur.

The exemplary method may further comprise inserting a spreading device into a joint space defined by the distal femur and a proximal femur of an operative leg to ascertain a distance between the distal femur and the proximal tibia. The distance comprises a medial distance and a lateral distance.

The exemplary method may further comprise using a traction device to pull the operative leg to apply traction to the proximal tibia or distal femur to expand the joint space.

The exemplary method may further comprise engaging a first tibial engagement member directly or indirectly to both the proximal tibia and the tibial portion of the linking drill guide.

In the exemplary method, the step of directly engaging the first tibial engagement member to the proximal tibia can comprise having the first tibial engagement member physically contact an anterior cortex of the proximal tibia.

In the exemplary method, the step of indirectly engaging the first tibial engagement member to the proximal tibia can comprise having the first tibial engagement member physically contact an intermediate tibial device. A portion of the intermediate tibial device can physically contact the proximal tibia.

In the exemplary method, the step of indirectly engaging the first tibial engagement member to the proximal tibia further can comprise having the first tibial engagement member physically contact an intermediate tibial device. A portion of the intermediate tibial device can physically contact a subsequent intermediate tibial device, and a portion of the subsequent intermediate tibial device can physically contact the proximal tibia.

The exemplary method may further comprise removing the linking drill guide from the first tibial engagement member, while leaving the first tibial engagement member directly or indirectly engaged to the proximal tibia.

The exemplary method may further comprise engaging a tibial resection guide to the first tibial engagement member.

The exemplary method may further comprise adjusting the posterior slope angle of the tibial resection guide relative to the position of the first tibial engagement member to define a desired resection slope.

The exemplary method may further comprise fixedly locking the tibial resection guide to the proximal tibia at the desired resection slope.

The exemplary method may further comprise resecting a tibial plateau of the proximal tibia at the desired resection slope.

The exemplary method may further comprise adjusting a height of the tibial resection guide relative to a top of the proximal tibia to accommodate a height of an endoprosthetic implant assembly.

The exemplary method may further comprise adjusting an internal/external angle of the tibial resection guide relative to the first tibial engagement member to define a desired internal/external resection angle.

The exemplary method may further comprise fixedly locking the tibial resection guide to the proximal tibia at the desired internal/external resection angle.

The exemplary method may further comprise resecting a tibial plateau of the proximal tibia at the desired internal/external resection angle.

The exemplary method may further comprise adjusting a medial/lateral position of the tibial resection guide relative to the first tibial engagement member to define a desired medial/lateral resection location.

The exemplary method may further comprise fixedly locking the tibial resection guide to the proximal tibia at the desired medial/lateral resection location.

The exemplary method may further comprise resecting a tibial plateau of the proximal tibia at the desired medial/lateral resection location.

It is to be understood that the present invention is by no means limited to the particular constructions and method steps herein disclosed or shown in the drawings, but also comprises any modifications or equivalents within the scope of the claims known in the art. It will be appreciated by those skilled in the art that the devices and methods herein disclosed will find utility.

What is claimed is:

1. A linking drill guide medical device comprising:
   a femoral portion, the femoral portion comprising a blade engaged to and extending from a posterior distal end of the femoral portion, the blade dimensioned to fit closely into a femoral resection slot of a distal femoral resection guide;
   a tibial portion, the tibial portion having tubes projecting from an inferior surface of the tibial portion, the tubes defining tibial reference holes; and
   a body connecting the femoral portion to the tibial portion, wherein a distal end of each of the tubes is recessed from a posterior distal end of the tibial portion of the linking drill guide medical device.

2. The linking drill guide medical device of claim 1 further comprising a handle engaged to the body.

3. The linking drill guide medical device of claim 1, wherein the inferior surface of the tibial portion aligns with a tibial resection plane when the linking drill guide medical device is in an engaged configuration.

4. A linking drill guide medical device comprising:
   a femoral portion, the femoral portion configured to engage a first femoral engagement member;
   a tibial portion, the tibial portion having a first arm oppositely disposed from a second arm to define a recess extending from a posterior distal side of the tibial portion and separating the first arm from the second arm, wherein each of the first arm and the second arm have a tube projecting from an inferior surface of the first arm and the second arm of the tibial portion, the tubes defining tibial reference holes; and
   a body connecting the femoral portion to the tibial portion, wherein a distal end of each of the tubes is recessed from a posterior distal end of the tibial portion of the linking drill guide medical device, and wherein the inferior surface of the first arm and the second arm of the tibial portion aligns with a tibial resection plane when the linking drill guide medical device is in an engaged configuration.

5. The linking drill guide medical device of claim 4, wherein the first femoral engagement member is selected from the group consisting essentially of: a femoral linking pin, a blade, a slot, a lip, a clamp, a hook, a protrusion, a recesses, a spike, a magnet, an orientation pin, and combinations thereof.

6. The linking drill guide medical device of claim 4 further comprising a handle engaged to the body.

* * * * *